(12) United States Patent
Fagan

(10) Patent No.: US 7,138,506 B2
(45) Date of Patent: Nov. 21, 2006

(54) UNIVERSAL MICROARRAY SYSTEM

(75) Inventor: John Fagan, Fairfield, IA (US)

(73) Assignee: Genetic ID, NA, Inc., Fairfield, IA (US)

(*) Notice: Subject to any disclaimer, the term of this patent is extended or adjusted under 35 U.S.C. 154(b) by 66 days.

(21) Appl. No.: 10/143,522

(22) Filed: May 9, 2002

(65) Prior Publication Data

US 2003/0003484 A1 Jan. 2, 2003

Related U.S. Application Data

(60) Provisional application No. 60/289,864, filed on May 9, 2001.

(51) Int. Cl.
  C07H 21/04 (2006.01)
  C12Q 1/68 (2006.01)
  C12M 1/00 (2006.01)
  C12M 1/36 (2006.01)

(52) U.S. Cl. ............... 536/23.1; 636/24.3; 435/6; 435/174; 435/283.1; 435/287.2

(58) Field of Classification Search .............. 435/6, 435/174, 283.1, 287.2; 536/23.1, 24.3
See application file for complete search history.

(56) References Cited

U.S. PATENT DOCUMENTS

| 5,407,799 A | 4/1995 | Studier ............ 435/6 |
| 5,424,186 A | 6/1995 | Fodor et al. ......... 435/6 |
| 5,445,934 A | 8/1995 | Fodor et al. ......... 435/6 |
| 5,654,147 A | 8/1997 | Wood et al. |
| 5,695,940 A | 12/1997 | Drmanac et al. ....... 435/6 |
| 5,716,785 A | 2/1998 | Van Gelder et al. ..... 435/6 |
| 5,744,305 A | 4/1998 | Fodor et al. ......... 435/6 |

(Continued)

FOREIGN PATENT DOCUMENTS

EP 0 558 671 B1 1/1991

(Continued)

OTHER PUBLICATIONS

Gerry et al "Universal DNA microarray method for multiplex detection of low abundance point mutations" J. Mol. Biol. 1999, 29 251-262.*

(Continued)

*Primary Examiner*—B J Forman
(74) *Attorney, Agent, or Firm*—Greenlee, Winner and Sullivan, P.C.

(57) ABSTRACT

The present invention provides a simple, cost-effective, universal method for determining and/or quantifying differences in nucleic acid levels between two or more test mixtures without prior knowledge of the sequence of the nucleic acids of interest. The method involves providing a universal microarray containing a plurality of spots, where each spot contains a plurality, or pool, of different oligonucleotide probes having at least three distinct portions: a universal sequence portion, a short central variable "wobble" sequence portion, and a unique sequence portion. A set of probes is synthesized such that the universal sequence portion is the same for every probe, and all possible permutations of the wobble sequence and unique sequence portions are represented in approximately equal concentrations in the set. The probes are pooled on the universal microarray such that probes in a given spot have the same unique portion and every permutation of the short wobble, while probes on different spots have different unique portions. Primers complementary to the universal and wobble portions of the probes are used to synthesize, for example, cDNA from an mRNA preparation. The cDNA is hybridized to the universal microarray, and through the use of differential labeling, is identified and/or quantified.

52 Claims, 7 Drawing Sheets

U.S. PATENT DOCUMENTS

| | | |
|---|---|---|
| 5,800,992 A | 9/1998 | Fodor et al. .................... 435/6 |
| 5,861,242 A | 1/1999 | Chee et al. ..................... 435/5 |
| 5,871,697 A | 2/1999 | Rothberg et al. .......... 422/68.1 |
| 5,871,928 A | 2/1999 | Fodor et al. .................... 435/6 |
| 5,891,636 A | 4/1999 | Van Gelder et al. ............ 435/6 |
| 5,922,550 A * | 7/1999 | Everhart et al. ........... 435/7.21 |
| 5,925,525 A | 7/1999 | Fodor et al. .................... 435/6 |
| 5,969,119 A | 10/1999 | Macevicz .................. 536/22.1 |
| 6,013,440 A * | 1/2000 | Lipshutz et al. ............... 435/6 |
| 6,025,136 A | 2/2000 | Drmanac ........................ 435/6 |
| 6,040,193 A | 3/2000 | Winkler et al. ............. 436/180 |
| 6,060,240 A | 5/2000 | Kamb et al. .................... 435/6 |
| 6,197,506 B1 | 3/2001 | Fodor et al. .................... 435/6 |
| 6,221,600 B1 | 4/2001 | MacLeod et al. .............. 435/6 |
| 6,236,945 B1 | 5/2001 | Simpson et al. .............. 702/20 |
| 6,261,776 B1 | 7/2001 | Pirrung et al. .................. 435/6 |
| 6,268,147 B1 | 7/2001 | Beattie et al. .................. 435/6 |
| 6,274,373 B1 | 8/2001 | Virtanen .................. 435/285.1 |
| 6,284,460 B1 | 9/2001 | Fodor et al. .................... 435/6 |
| 6,297,006 B1 | 10/2001 | Drmanac et al. .............. 435/6 |
| 6,306,643 B1 | 10/2001 | Gentalen et al. |
| 6,309,822 B1 | 10/2001 | Fodor et al. .................... 435/6 |
| 6,344,316 B1 | 2/2002 | Lockhart et al. ............... 435/6 |
| 6,346,413 B1 | 2/2002 | Fodor et al. ............. 435/287.2 |
| 6,355,419 B1 | 3/2002 | Alfenito ........................ 435/6 |
| 6,355,423 B1 | 3/2002 | Rothberg et al. ............... 435/6 |
| 6,355,431 B1 | 3/2002 | Chee et al. ..................... 435/6 |
| 6,355,432 B1 | 3/2002 | Fodor et al. .................... 435/6 |
| 6,361,944 B1 | 3/2002 | Mirkin et al. ................... 435/6 |
| 6,361,947 B1 | 3/2002 | Dong et al. ..................... 435/6 |
| 6,582,908 B1 * | 6/2003 | Fodor et al. .................... 435/6 |
| 6,852,490 B1 | 2/2005 | Gentalen |
| 6,864,052 B1 | 3/2005 | Drmanac et al. |
| 2001/0007747 A1 | 7/2001 | Bochkariov et al. ........... 435/6 |
| 2001/0007985 A1 | 7/2001 | Rothberg et al. ............... 707/1 |
| 2001/0031468 A1 | 10/2001 | Chenchick et al. ............. 435/6 |
| 2001/0046681 A1 | 11/2001 | Senapathy ..................... 435/6 |
| 2001/0053519 A1 | 12/2001 | Fodor et al. .................... 435/6 |
| 2002/0012913 A1 | 1/2002 | Gunderson et al. ............ 435/6 |
| 2002/0012926 A1 | 1/2002 | Quake et al. ................... 435/6 |
| 2002/0012940 A1 | 1/2002 | Lockhart et al. ............... 435/6 |
| 2002/0022261 A1 | 2/2002 | Anderson et al. ......... 435/287.2 |

FOREIGN PATENT DOCUMENTS

| | | |
|---|---|---|
| EP | 1 180 548 A2 | 2/2000 |
| EP | 0 742 837 B1 | 6/2001 |
| EP | 0 834 575 B1 | 11/2001 |
| EP | 0 834 576 B1 | 1/2002 |
| WO | WO 93/20096 | 10/1993 |
| WO | WO95/11995 | 5/1995 |
| WO | WO 97/27317 | 7/1997 |
| WO | WO 97/31256 | 8/1997 |
| WO | WO 99/07896 | 2/1999 |
| WO | WO 99/09217 | 2/1999 |
| WO | WO 99/28505 | 6/1999 |
| WO | WO 00/03038 | 1/2000 |
| WO | WO 00/22171 | 4/2000 |
| WO | WO 00/58516 | 5/2000 |
| WO | WO 00/63437 | 10/2000 |
| WO | WO 00/75377 | 12/2000 |
| WO | WO 01/29261 | 4/2001 |
| WO | WO 01/57269 | 8/2001 |
| WO | WO 01/59161 | 8/2001 |
| WO | WO 02/14534 | 2/2002 |
| WO | WO 02/16649 | 2/2002 |
| WO | WO 02/18655 | 3/2002 |

OTHER PUBLICATIONS

Schepinov et al "Steric facotrs influencing hybrization of nucleic acids to oligonucleotide arrays" Nucleic Acid Research, 1997, 25(6): 1155-1161.* van Dam, R.M. et al. (2002) "Gene Expression Analysis with Universal n-mer Arrays" *Genome Research* 12:145-152.

* cited by examiner

UNIVERSAL MICROARRAY SYSTEM

CROSS-REFERENCE TO RELATED APPLICATIONS

This application is claims priority under 35 U.S.C. §119 (e) to U.S. Provisional application Ser. No. 60/289,864 filed May 9, 2001, which is incorporated in its entirety by reference herein.

FIELD OF THE INVENTION

The present invention relates to the field of detection of specific nucleic acid sequences from test mixtures containing large numbers of such sequences, such as those derived from the full genetic complement of mRNAs or genes in a prokaryotic or eukaryotic cell.

BACKGROUND OF THE INVENTION

Recent research has revealed that the number of genes present in the human genome is between 30,000 and 50,000, and that the number of genes present in the genome of Arabidopsis, the first higher plant genome to be fully sequenced, is around 40,000 (Mayer, K., et al. Nature. Dec. 16, 1999;402(6763): 731–2). The genomes of simpler organisms are smaller, ranging down to a few thousand genes in bacteria, such as *Escherichia coli*.

Multicellular organisms contain many different cell types, each with different functional characteristics. All of these different cell types contain the same databank of genetic information and roughly the same number of genes. Thus, for example, if one cell derived from an organism has a genetic complement made up of 40,000 genes then most all cells derived from the same organism are likely to have the same set of 40,000 genes. However, not all of these genes are expressed in every cell type of the organism. Certain combinations of genes are expressed in different cell types. For example, in animals, a certain combination of genes is expressed in liver cells, a different combination of genes in brain cells, etc. It is the profile of genes expressed in any given cell type that determines the functional characteristics of that cell type. Likewise, cells adapt their style of functioning to respond to inputs from the environment and from other parts of the physiology of the organism. In most cases this adaptation involves turning some genes on and other genes off. For instance, a normal liver cell will express a very different set of genes than would be expressed by a liver tumor cell, although some genes may be expressed by most or all cells of a given multicellular organism. Furthermore, environmental effects, such as extracellular signals, can induce a change in the number and types of, or the relative levels of genes expressed in a given cell type.

Understanding which genes are expressed in which cell types and under which conditions is key to understanding living systems. More practically, a knowledge of which genes are expressed at higher or lower levels in disease states provides data that can be extremely valuable in identifying new drug targets, and ultimately new pharmaceuticals or other therapeutics. Information about gene expression is also useful in tailoring therapeutic approaches for individual patients based on their own genetic expression response to different pharmaceuticals, diet, or environmental stimuli.

Current approaches to measuring gene expression (e.g. Northern blot hybridzation, dot blot hybridization, in vitro translation and immunoprecipitation, and hybridization with microarrays constucted with probes designed to detect specific mRNA, usually require prior knowledge of what genes are of interest in order to design sequence-specific probes and primers (Sambrook, et al., Molecular Cloning: A Laboratory Manual, Third Edition, Cold Spring Harbor, N.Y. (2000)). These targeted approaches may miss important information about altered gene expression by never studying expression of unknown genes, or genes not thought to be of great importance. For example, in humans there are currently believed to be about 50,000 genes that can be expressed in any given cell type. Thus, to determine the active complement of genes in a given cellular genome, one needs to efficiently scan a given cell type quantitatively, or at least semi-quantitatively, for all of the active, i.e. expressed, genes.

A need thus exists in the field of gene expression analysis for methods and assay configurations to screen all active genes in different cells under different conditions or states for possible changes in gene expression. Systems are needed for monitoring and analysis of gene expression preferably screen gene expression universally without regard to cell type or species.

The use of very high density oligonucleotide arrays is one technology area that may be exploited for just such a universal system. U.S. Pat. No. 6,344,316 reports the use of such high density arrays for "generic difference screening" of gene expression. The screening method of this patent employs an array of oligonucleotide probes, wherein the location and sequence of each different probe is unique and known and wherein the probes are not chosen to hybridize to nucleic acid derived from particular pre-selected genes. Probe oligonucleotides are described as chosen by random selection, haphazard selection, nucleotide composition biased selection, or as all possible oligonucleotide combinations of a chosen oligonucleotide length. For example, $4^8$, or 65,536 distinct, locatable array spots are required to encompass all possible permutations of 4 bases (A, G, C and T) in an 8 base oligonucleotide probe. While containing an enormous amount of information about the sequence of oligonucleotides bound to these probes, arrays comprising such a large number of different probe spots containing unique probes are very costly.

However, an exhaustive array that would be effective in stringent discrimination of single base pair mismatches would comprise a very large plurality of features. Specifically, oligonucleotides of between 11 and 20 base pairs in length would be required to achieve stringent discrimination of single base pair mismatches. An exhaustive microarray employing 11 base oligonucleotides would have $4^{11}=4.2\times 10^6$ spots. An exhaustive microarray employing 20 base oligonucleotides would comprise $4^{20}=1.1\times 10^{12}$ spots. Both of these designs are far too large for practical use. Moreover, such microarrays would be prohibitively expensive to manufacture.

The present invention provides an integrated system of design for probes, primers, and microarrays, and strategies for labeling nucleic acids. The system generates microarrays that address the problems posed above. The microarrays of this invention (1) are capable of exhaustive screening of the gene expression profile of unknown cell type or organism, and (2) are economical to manufacture.

BRIEF SUMMARY OF THE INVENTION

The present invention is based on the use in microarray assays of selected oligonucleotide probes having at least three distinct portions: a universal sequence portion, a short central variable wobble sequence portion, and a unique sequence portion. A set of probes is synthesized such that the universal sequence portion is the same for every probe, and all possible permutations of the wobble sequence and unique sequence portions are represented in approximately equal concentrations in the set. This set of probes is attached to a substrate to form an array in such a way that defined spots on the array contain a defined plurality, or pool, of oligonucleotides. Specifically, the probes within a single spot have, in addition to the universal sequence portion, all permutations of the variable sequence portion, and just one of all the permutations of the unique sequence portion. Spots on the array differ from each other in that the unique sequence portion of probes within each spot differs. The sequence of all probes in all spots are known.

For the assays of this invention, a set of primers is also synthesized such that each primer has at least two portions: a universal portion that is complementary to the universal portion of the probe set, and all permutations of the central wobble sequence. These primers are used to generate populations of oligonucleotides representative of expressed genes that will bind to probes in the array. For example, the primers are used to synthesize cDNA from sample mRNA. The synthesized cDNA is differentially labeled according to the primer from which it was synthesized, before or after hybridization to the microarray. In this manner, hybridization of cDNAs from different test mixtures to a location on the microarray can be used to measure relative gene expression or gene expression profiles. In addition, the cDNAs bound to different locations on the microarray can be traced back to a specific primer of known sequence. This sequence information can be used to determine the sequence of the mRNA from which the cDNA was synthesized.

Primers of this invention are typically used to synthsize cDNA from messenger RNA. However, those of ordinary skill in the art will recognize that such primers may be used to synthesize copies of any oligonucleotide and as such the methods herein can be applied to detect and determine the relative amount of any oligonucleotides in one or more test mixtures.

This invention provides probes, and strategies for the selection and synthesis of probes. The invention further provides strategies for the design of universal microarrays using the probes of this invention such that the number of spots on a microarray is minimized to reduce cost of manufacture.

This invention further provides primers that are useful in the synthesis of oligonucleotides that are complementary to the probes on the universal microarray. These primers are also universal in that they are designed such that a portion of the primer is complementary to nearly every oligonucleotide in a test mixture. For example, primers may be designed to be complementary to every gene in a target genome, or every expressed gene in a test mixture.

The invention further provides methods for using the probes and primers of this invention to determine the relative levels of sample oligonucleotides, e.g. mRNA, in two or more test mixtures. For example, methods of determining relative gene expression in test mixtures of mRNA originating from different cell types or different cell states, are provided that use the primers of this invention to synthesize cDNA from mRNA in separate test mixtures. The synthesized cDNA, with the primers still attached, is interrogated with the microarray containing probes of this invention, under suitable hybridization conditions. Bound cDNA (and ultimately the mRNA from which it was synthesized) is then identified and/or quantified.

This invention also provides kits for the measurement of gene expression. The kits may contain any or all of the following: probes, primers, microarrays (with or without pre-attached probes), labels, mRNA prep reagents and buffers, cDNA synthesis reagents and buffers, hybridization reagents and buffers, and instructions for the use of the materials in the kit and operation of the assays.

DEFINITIONS

The following terms are intended to have the following general meanings as they are used herein:

An "array" or "microarray", terms used synonymously herein to refer to a plurality of oligonucleotides attached to one or more distinguishable spots on a substrate. A microarray may comprise a single substrate or a plurality of substrates, for example a plurality of beads or microspheres. A "copy" of a microarray contains the same types and arrangements of oligonucleotides.

A "universal array" or "universal microarray" is one or more microarrays that comprise a sufficient number of oligonucleotide probes arranged in a plurality of spots such that there is a very high probability, preferably a probability of 90% or more, that every expressed gene in a sample will be bound to at least one spot on the microarray.

The term "substrate" refers to any solid support to which nucleic acids may be attached. The substrate material may be modified, covalently or otherwise, with coatings or functional groups to facilitate binding of nucleic acids. Suitable substrate materials include polymers, glasses, semiconductors, papers, metals, gels and hydrogels among others. Substrates may have any physical shape or size, e.g., plates, strips, or microparticles. In preferred embodiments the substrates are plates typically less than 1 $cm^2$ in area.

The term "spot" refers to a distinct location on a substrate to which oligonucleotide probes of known sequence or sequences are attached. A spot may be an area on a planar substrate, or it may be, for example, a microparticle distinguishable from other microparticles.

The term "nucleotide sequence" refers to either a homopolymer or a heteropolymer of deoxyribonucleotides, ribonucleotides or other nucleic acids. As used herein, the term "nucleotide" is used generally herein to refer to the monomer components of nucleotide sequences even though the monomers may be nucleoside and/or nucleotide analogs, and/or modified nucleosides such as amino modified nucleosides in addition to nucleotides. In addition, "nucleotide" includes non-naturally occurring analog structures. Thus for example the individual units of a peptide nucleic acid, each containing a base, are referred to herein as a nucleotide.

The term "nucleic acid" means at least two nucleotides covalently linked together. An oligonucleotide may be optionally derived from natural sources, but is often, especially for purposes of the present invention, synthesized chemically. A nucleic acid of the present invention will generally contain phosphodiester bonds, although in some case, as outlined below, nucleic acid analogs are included that may have alternate backbones, comprising, for example, phosphoramide (Beaucage et al., Tetrahedron 49(10):1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al., Chem. Left. 805 (1984), Letsinger et al., J. Am. Chem. Soc. 110:4470 (1988); and Pauwels et al., Chemica Scripta 26:141 (1986)), phosphorothioate (Mag et al., Nucl. Acids Res. 19:1437 (1991); and U.S. Pat. No. 5,644,048), phosphorodithioate (Briu et al., J. Am. Chem. Soc. 111:2321

(1989), O-methylphosphoroamidite linkages (see Eckstein, Oligonucleotides and Analogues: A Practical Approach, Oxford University Press), and peptide nucleic acid backbones and linkages (see Egholm, J. Am. Chem. Soc. 114: 1895 (1992); Meier et al., Chem. Int. Ed. Engl. 31:1008 (1992); Nielsen, Nature, 365:566 (1993); Carlsson et al., Nature 380:207 (1996), all of which are incorporated by reference). Other analog nucleic acids include those with positive backbones (Denpcy et al., Proc. Natl. Acad. Sci. USA 92:6097 (1995); non-ionic backbones (U.S. Pat. Nos. 5,386,023, 5,637,684, 5,602,240, 5,216,141 and 4,469,863; Kiedrowshi et al., Angew. Chem. Intl. Ed. English 30:423 (1991), Letsinger et al., J. Am. Chem. Soc. 110:4470 (1988); Letsinger et al., Nucleoside & Nucleotide 13:1597 (1994); Chapters 2 and 3, ASC Symposium Series 580, "Carbohydrate Modifications in Antisense Research", ed. Y. S. Sanghui and P. Dan Cook; Mesmaeker et al., Bioorganic & Medicinal Chem. Left. 4:395 (1994); Jeffs et al., J. Biomolecular NMR 34:17 (1994); Tetrahedron Lett. 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", ed. Y. S. Sanghui and P. Dan Cook. Nucleic acids containing one or more carbocyclic sugars are also included within the definition of nucleic acids and oligonucleotide (see Jenkins et al., Chem. Soc. Rev. (1995) pp. 169–176). Several nucleic acid analogs are described in Rawls, C & E News Jun. 2,1997 page 35. All of these references are hereby expressly incorporated by reference.

As will be appreciated by those in the art, all of these nucleic acid analogs may find use in the present invention. In addition, mixtures of naturally occurring nucleic acids and analogs can be made.

Peptide nucleic acids (PNA) are included as nucleic acids, as are peptide nucleic acid analogs. PNA is synthesized using the techniques outlined in Will et al., Tetrahedron 51(44): 12069–12082 (1995), and Vanderlaan et al., Tett. Let. 38:2249–2252 (1997), both of which are expressly incorporated in their entirety. The PNA backbone is substantially non-ionic under neutral conditions, in contrast to the negatively charged phosphodiester backbone of naturally occurring nucleic acids. This results in two advantages. First, the PNA backbone exhibits improved hybridization kinetics. PNAs have larger changes in the melting temperature(Tm) for mismatched versus perfectly matched basepairs. DNA and RNA typically exhibit a 2–4° C. drop in Tm for an internal mismatch, while the drop in Tm for PNA is 7–9° C. This allows for better detection of mismatches. Second, due to the non-ionic nature of DNA, hybridization is relatively insensitive to salt concentration, which increases the range of conditions under which the invention can operate successfully.

Nucleic acids may be single stranded or double stranded, as specified, or contain portions of both double stranded or single stranded sequence. The nucleic acid may be DNA, both genomic and cDNA, RNA or DNA-RNA hybrids where the nucleic acid contains any combination of deoxyribo- and ribo-nucleotides, and any combination of bases, including uracil, adenine, thymine, cytosine, guanine, inosine, xathanine and hypoxathanine, etc.

An "oligonucleotide" is a nucleic acid, or nucleotide, sequence comprised of tow or more nucleotide bases, as the term nucleotide is used most generally herein. An oligonucleotide may be optionally derived from natural sources, but is often, especially for purposes of the present invention, synthesized chemically. An oligonucleotide may also include natural (i.e. A, G, C or T) or modified bases. A, G, C and T as used herein refer to natural bases or their modified forms so long as the modified forms do not interfere with the methods disclosed herein. The bases in an oligonucleotide may also be joined by linkages other than a phosphodiester bond as long as the altered linkage does not interfere with the function of the oligonucleotide (e.g. as a primer for CDNA synthesis), or with its hybridization to complementary oligonucleotides. All alterations of any of the bases of or backbone linkages in any described oligonucleotides are included in this invention.

Reference to a "DNA sequence" can include both single stranded and double stranded DNA. A specific sequence, unless the context indicates otherwise, refers to the single strand DNA of such sequence, the duplex of such sequence with its complement (double stranded DNA) and/or the complement of such sequence.

The term "DNA segment" refers to a DNA polymer, in the form of a separate fragment or as a component of a larger DNA construct, which has been derived either from isolated DNA or synthesized chemically or enzymatically such as by methods disclosed elsewhere herein.

As used herein, the terms "portion" and "segment," and when used in relation to polynucleotides, especially oligonucleotides, such as the probes described herein, that are useful in practicing the present invention, are to be deemed synonymous.

The term "complementary" refers to the ability of two nucleotide sequences to bind sequence-specifically to each other by hydrogen bonding through their purine and/or pyrimidine bases according to the usual Watson-Crick rules for forming duplex nucleic acid complexes. It can also refer to the ability of nucleotide sequences that may include modified nucleotides or analogues of deoxyribonucleotides and ribonucleotides to bind sequence-specifically to each other by other than the usual Watson Crick rules to form alternative nucleic acid duplex structures The term "hybridization" refers to the process by which two nucleotide sequences complementary to each other bind together to form a duplex sequence or segment.

The term "duplex" refers to a structure formed as a result of hybridization of two complementary sequences of nucleic acids. Such duplexes can be formed by the complementary binding of two DNA segments to each other, two RNA segments to each other, or of a DNA segment to an RNA segment, the latter structure termed a hybrid duplex. Either or both members of such duplexes can contain modified nucleotides and/or nucleotide analogues as well as nucleoside analogues. As disclosed herein, such duplexes are formed as the result of binding of one or more probes to a sample sequence, such as the cDNA sequences formed according to the processes of the present invention.

The terms x-mer, n-mer, z-mer, t-mer and the like refer to a nucleotide segment x, n, z, and t nucleotides in length, where x, n, z and t are integers. The terms "octanucleotide," "octamer" or "8-mer" are synonymous and refer to a nucleotide segment of 8 nucleotide residues in length, such as one or more of the primers used in the methods disclosed herein. Similarly "hexanucleotide," "hexamer," and "6-mer" refer to a nucleotide segment of 6 nucleotides in length. The integer 6, used in this example, can be replaced with any integer and the first syllable of "hexanucleotide" and "hexamer" replaced with the appropriate syllable to refer to a nucleotide whose length is specified by said integer. The term "14-mer" refers to a nucleotide segment of 14 nucleotide residues in length, such as one or more of the probes used in the apparatus and methods disclosed herein.

The term "universal n-mer", for instance "universal hexamer" or "universal 6-mer", refers to a nucleotide segment n nucleotide residues in length, which is commonly part of a probe used herein, and which has a nucleotide sequence that is the same among all probes present on a particular microarray or chip. The complement of a universal n-mer is commonly part of the primers used in synthesizing the sample sequences that are to be interrogated by the corresponding microarray.

The term "unique z-mer", for instance "unique hexamer", refers to a nucleotide segment of z nucleotide residues in length, which is commonly part of a probe used herein, and which has a nucleotide sequence that is the same among all probes present in a particular pool or area on a particular microarray or chip but is different for probes present in different pools of the same microarray or chip.

The term "all permutations", as in "all $4^x$ permutations of the nucleic acid bases A, G, C, and T in an x-mer" refers to every possible non-degenerate combination of the 4 nucleic acid bases in an oligonucleotide, or oligonucleotide portion.

A "pool" as used herein to refer to "a pool of oligonucleotides" is, for example, a plurality of different oligonucleotides grouped together. For example, a pool may be on a single spot on a microarray, or may be grouped in a single container.

"Pooling" refers to, for example, the combining of individual members of a set or subset.

The term "primer" means a short nucleic acid sequence that can be paired with a complementary strand of DNA or RNA and provides a free 3'OH end at which a DNA polymerase can start synthesis of a nucleic acid chain. In the present invention, such primers are commonly 8 nucleotide residues or longer in length (i.e., an octamer or higher oligomer) and used to initiate or prime the synthesis of a cDNA on a mRNA (messenger RNA) template by means well known in the art for preparing such cDNA products. According to this invention, sets of primers commonly comprise the complement of a probe universal n-mer and all possible permutations of the probe variable x-mer.

The term "probe" refers to a short piece of DNA, such as an oligonucleotide, capable of hybridizing to, for example, sample oligonucleotide containing a sequence complementary to that of the probe, and wherein said probe possesses a nucleotide sequence sufficiently distinct to selectively bind to the sample oligonucleotide when the latter is present in a test mixture containing more than one other oligonucleotide sequence. For use in the methods and apparatus of the present invention, such probes are commonly about 11–20 bases in length, and preferably 14 bases though they may be longer or shorter. The probes useful in forming the apparatus of the present invention, in their most preferred embodiment, commonly comprise a universal n-mer at one end of the probe, a unique z-mer at the other end of the probe and all permutations of a variable x-mer central to the unique and universal hexamers.

The term "matching", as in "matching probes" or "matching primers" refers to probes and primers whose segment sequences are designed to be complementary, as disclosed herein.

The terms "sample sequence" or "sample oligonucleotide" refer to a polynucleotide, including a single stranded DNA or RNA, present in a test mixture that is capable of selectively hybridizing to a probe sequence as described herein. For use with the present invention, such sample sequences are commonly part of a cDNA synthesized on an mRNA template, said synthesis employing primers disclosed herein.

The term "recovering" is used herein to refer to the isolation of sample sequences from other components that may be present in a given test mixture. Methods of recovering sample sequences are known in the art.

The terms "approximately equal", and "approximately equimolar" when used to refer to probes, primers, cDNA populations, mRNA populations, and the like, are used herein to mean that the probes, primers, and populations are present in approximately equal amounts such that differences between samples or test mixtures being compared are of sufficiently small magnitude that the differences have negligible influence on the outcome of the measurements undertaken, and thus do not prevent the use of the systems and methods of this invention for determining, for example, relative gene expression between test mixtures.

DETAILED DESCRIPTION OF THE INVENTION

Figure 1:
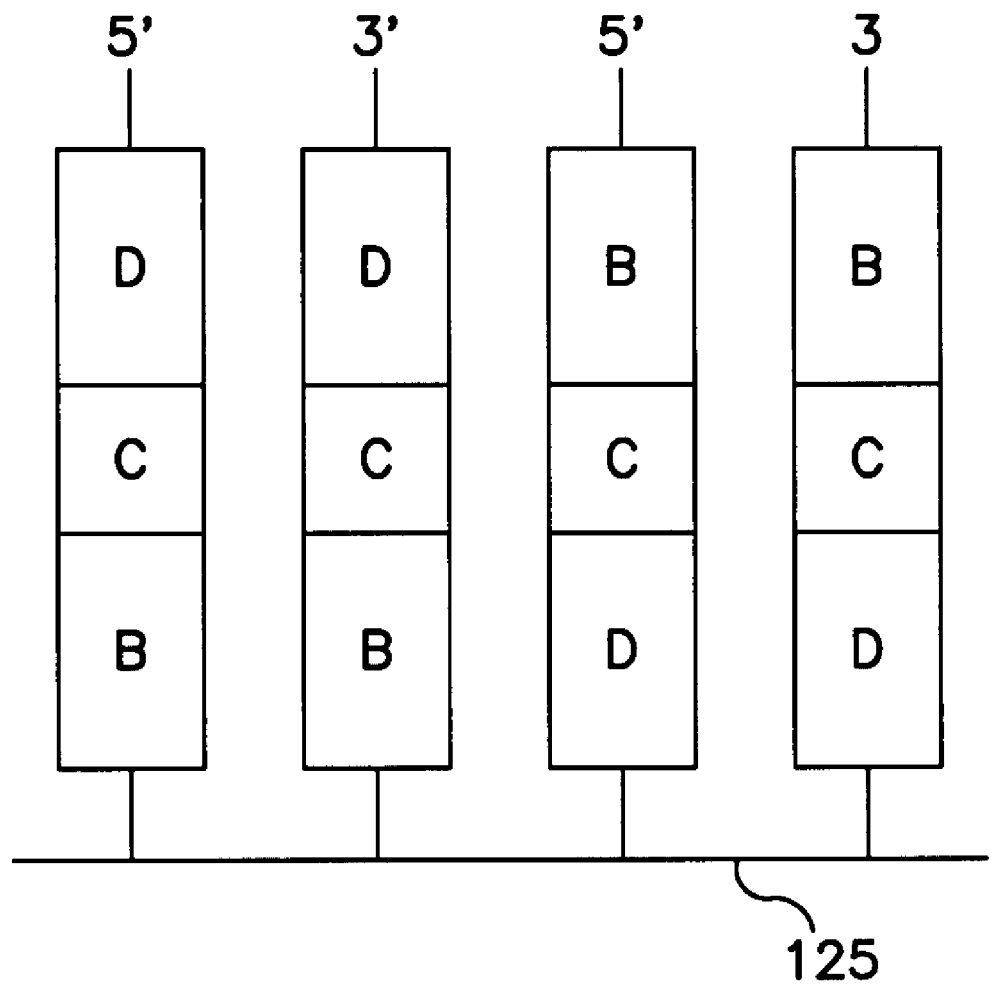
FIG. 1 illustrates some of the ways in which probes of this invention may be attached to a solid support.

The universal microarray system of the present invention finds use in a number of different applications including examining effects of disease states and physiological states of specific cell and tissue types and determining the effects of a drug or other compound on gene expression. One such non-limiting application is determination of the gene expression profile of a given cell or tissue type, such as in situations where:

1. A selection of oligonucleotide probes are spotted onto a glass slide, such as a microscope slide, the analytical power of a given microarray depending on the selection of probe molecules that one has available to spot on the slide.

2. Messenger RNA (mRNA) is isolated from the cell type of interest, and DNA copies of this mRNA population are synthesized enzymatically. These DNA copies are called cDNA molecules. The synthesis is done in such a way that the cDNA molecules are labeled with a fluorescent dye, a microparticle, a radiolabel, or some other detectable label.

3. The microarray is exposed to a solution containing the cDNA population. This is done under conditions in which cDNAs will hybridize to the probe molecules that are immobilized to the mircoarray, if the immobilized molecules are complementary in sequence to the cDNAs.

4. The mircoarray is washed to remove cDNA that has not hybridized specifically to the probe molecules spotted on the chip, and the chip is scanned to locate spots within the array to which specific cDNAs have hybridized and wherein relative intensity of the fluorescence emitted by different hybridized sequences is indicative of the relative expression of the corresponding genes.

While the universal microarray system disclosed herein makes use of this basic assay procedure, the system of the present invention differs from other microarrays in the use of a unique strategy that integrates three interdependent elements: (1) design of the oligonucleotide probes that are bound to the mircoarray; (2) the grouping or pooling of those probes and their arrangement on the microarray; and (3) primer design and strategy for generating the fluorescently-labeled cDNA.

In a preferred embodiment, the result is a microarray with less than 5000 spots that can differentiate more than 65,000 different mRNA/cDNA species. The microarrays of the present invention can contain less than 1000 spots, less than 500 spots, less than 100 spots or less than 40 spots. It is capable of economically achieving this level of discrimination for any population of mRNAs, from virtually any cell type of any species. This chip can be used to economically, yet exhaustively characterize the population of mRNAs present in any cell type or tissue from any species, and compare the expression profile of that cell type to that of any other.

The strategy employed by the microarray of the present invention has the following salient features. It is universal in the sense that the microarray, once developed, is useable in profiling the mRNA expression pattern, and changes therein, of essentially any genome. Thus, the microarray of the present invention is general in its application and is not genome specific. It provides a semi quantitative or quantitative evaluation or profile of all of the mRNAs expressed in a given cell type or tissue, as long as that population contains fewer mRNAs than the number of different probes on the microarray. Such a system should be capable of comparing the expression profiles of the same tissue/cell type under many different conditions, or of different tissue or cell types, and can also be used for other purposes.

Because the universal microarray system of the present invention is truly universal in its application to different species, tissues, and cell types, it offers significant advantages over target-specific microarray technologies available in the marketplace today. In addition, the microarray allows the parsimonious, economical, and efficient screen for changes in expression of all mRNAs encoded in the genome of a given species. In particular, because the same universal microarray can be used for almost all gene expression studies or other applications, it can be mass produced, greatly reducing the cost of manufacture and thus making exhaustive gene expression profiling widely accessible for both diagnostic and research applications.

In one aspect, the present invention relates to a device or apparatus for performing an assay comprising a microarray containing a suitably large number of spots, each spot having a different oligonucleotide probe pool, each of said different pools including a plurality of different oligonucleotides, each of the different oligonucleotides in each of the different pools comprising first, second and third portions, wherein the portions are identical or different from each other depending on the location on the array of the spot of which they are a part, and thus sequence and location of each oligonucleotide is known.

In its most general embodiment, the present invention relates to the preparation and placement of oligonucleotide probes at specific locations on an array, or microarray, or "chip," for detection of specific oligonucleotide sequences, such as those present in a population of cDNAs generated from a population of mRNAs isolated from a given cell type or tissue. Thus, in one aspect, the present invention relates to methods and apparatus for preparing such microarrays and thereby facilitating identification of one or more sequences derived from a test mixture, such as a test mixture comprising the complement of mRNAs present in a cell, and detecting and identifying such a sequence in the presence of other sequences in the test mixture. Methods and apparatuses of this invention are particularly useful for determination of the relative amounts of oligonucleotides, for example mRNA, and thus the relative expression of a given sequence in samples under study.

In addition, the present invention provides an apparatus and methods for distinguishing or differentiating among all genes present in a genome, and differentiating among and quantifying, or semi-quantifying, the levels of all members of the mRNA population expressed in a given cell type, tissue type, etc. (called the expressed genome complement of that cell type, tissue, etc.), or all cDNAs derived from said mRNA population. The present invention finds special use in the area of screening for nucleotide sequences present in a target genome, and especially in screening for relative levels of expression of the mRNAs encoded by such genes.

In accordance with the foregoing, the present invention provides methods and apparatus for the preparation and use of a substrate having a plurality of oligonucleotide sequences, or probes, or probe sequences, in predefined regions of said substrate, such as a solid substrate or solid support. This substrate with attached probes, called a "microarray" or "chip," is used in screening a variety of polynucleotides as ligands for binding with specific probe sequences. In forming such an array, it may be beneficial to attach said probes to said substrate using other linking structures, such as various linking molecules, but in all cases such linkers will in no way detract from the ability of the probes to hybridize to complementary oligonucleotide sequences. Methods of forming such arrays are described in the literature. (See, for example, U.S. Pat. No. 5,143,854.) As used in the present invention, such microarrays will commonly be of the order of about 1 square centimeter. Smaller or larger arrays are technologically possible and may find use where the genome to be studied is relatively small, perhaps 1,000 genes or less, or is relatively large, possibly 100,000 genes or more.

In one aspect, the present invention relates to a device or apparatus for performing an assay comprising a microarray having a suitably large number of different spots. Each spot comprises a "pool" of oligonucleotides, and each pool comprises of a plurality of different oligonucleotide probes having the general form:

B-C-D wherein
a) portion B is a unique z-mer comprising from about 5 to about 8 nucleotide bases such that all $4^z$ permutations of A, G, C, and T are represented in said plurality of oligonucleotide probes and only one of said $4^z$ permutations is present in each spot;
b) portion C is a variable x-mer comprising at least 1 nucleotide base such that all $4^x$ permutations of A, G, C, and T are represented in said plurality of oligonucleotide probes and all $4^x$ permutations are present in every spot in about equal concentrations;
c) portion D is a universal n-mer comprising from about 5 to about 8 nucleotide bases that is the same for every probe.

B, C, and D are joined in either the 5'-3' or the 3'-5' direction and either end may be attached to the microarray substrate (FIG. 1). In preferred embodiments, B and D are hexamers and C is a dimer. Also in preferred embodiments, B, C and D are joined in the 5' to 3' direction and the probes are attached to the microarray substrate at the 3'-OH end.

In other embodiments of this invention, the oligonucleotide probes further comprise a fourth portion E that is a t-mer of about 1 to about 4 nucleotides adjacent to portion B or portion D at either end of each oligonucleotide probe, wherein the sequence of portion E is variable within any given spot on the universal microarray such that all possible $4^r$ permutations of A, G, C, and T are represented within any given spot for each form of B-C-D located within that spot. In preferred embodiments, E is adjacent to D at the 3' end of the probe, or E is adjacent to B at the 5' end of the probe, when B, C and D are joined in the 5' to 3' direction and attached to the substrate the 3' end.

In preferred embodiments, the length of the oligonucleotide probe, including all portions, is between 11 and 20 bases.

The probes described above may also comprise a linker group A, through which the probe is attached to the solid substrate of the array. Linking moieties relying on a variety of covalent and noncovalent interactions with the substrate are well known in the art and method employing such linker groups can be readily applied to the microarrays of this invention.

Substrates useful in the preparation of the microarrays of this invention are made from any material to which oligonucleotides useful in the invention as probes can be attached in a defined manner, and can include such materials as glass, polymers, metals, semiconductors, papers, hydrogels, and the like. Substrates may be bare, or may have additional coatings on them, or may be chemically modified to facilitate binding with the probes. Such coatings and modifications are well known in the art.

In further embodiments, spots on the microarray may be segmented, or grouped, into sets of spots having probes with similar properties. Such properties may be related to the strength of hybridization of the probes to complementary sample nucleic acids. For example, spots may be grouped according to their calculated melting temperature for hybridization with their complements. Such segmentation may be useful for imposing different hybridization conditions for different probe types. Segmentation may comprise localization of particular probes to an area on the microarray substrate, or the physical segmentation of groups of probes on separate substrates. The groups of separated spots, in either case, may be referred to as subarrays.

Figure 2:
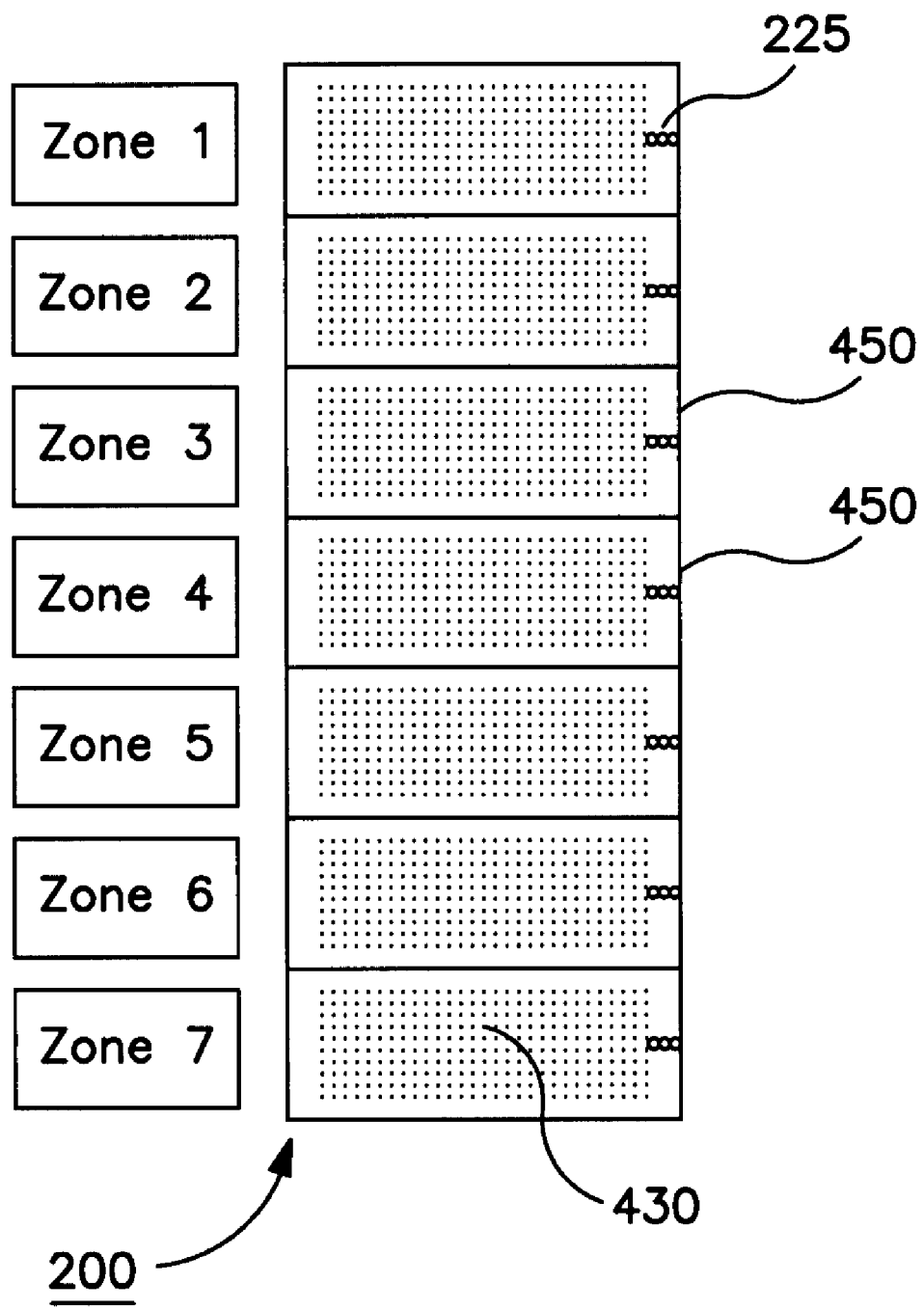
FIG. 2 illustrates a top view of a microarray comprising seven zones.

For example, the 4096 pools of oligonucleotide probes, each pool comprising 16 different oligonucleotide probes each having identical universal hexamer and identical unique hexamer, but each differing from the other 15 members of the pool by having a different central variable dinucleotide, as described above, are placed in 7 groups, according to the percentage of G and C in the variable hexamer for each pool. In this example, each group comprises approximately 585 probe pools. All members of said 7 groups are arrayed (spotted) on the microarray substrate in close proximity, as is known in the art, wherein each of said 7 groups is located in a distinct zone on the chip, separated from the other zones on the chip, as depicted in FIG. 2.

In one embodiment, seven copies of the microarray having the 7 zones arrayed on it, are hybridized with fluorescently labeled sample oligonucleotides. Each of the 7 copies is held at a temperature optimal for hybridization of one group of the 7 groups of probe pools to the sample oligonucleotides, thereby affording optimal discrimination of single base-pair mismatches between the probe oligonucleotides located within said zone and sample oligonucleotides applied to the microarray. For instance, for a set of 4096 pools, all having a universal hexamer that is 50% GC content, the seven copies of the chip could be hybridized at a range of temperatures corresponding to the percentage of GC in the unique hexamer. Methods for calculating hybridization temperature for given nucleic acid contents are well known in the art.

Figure 3:
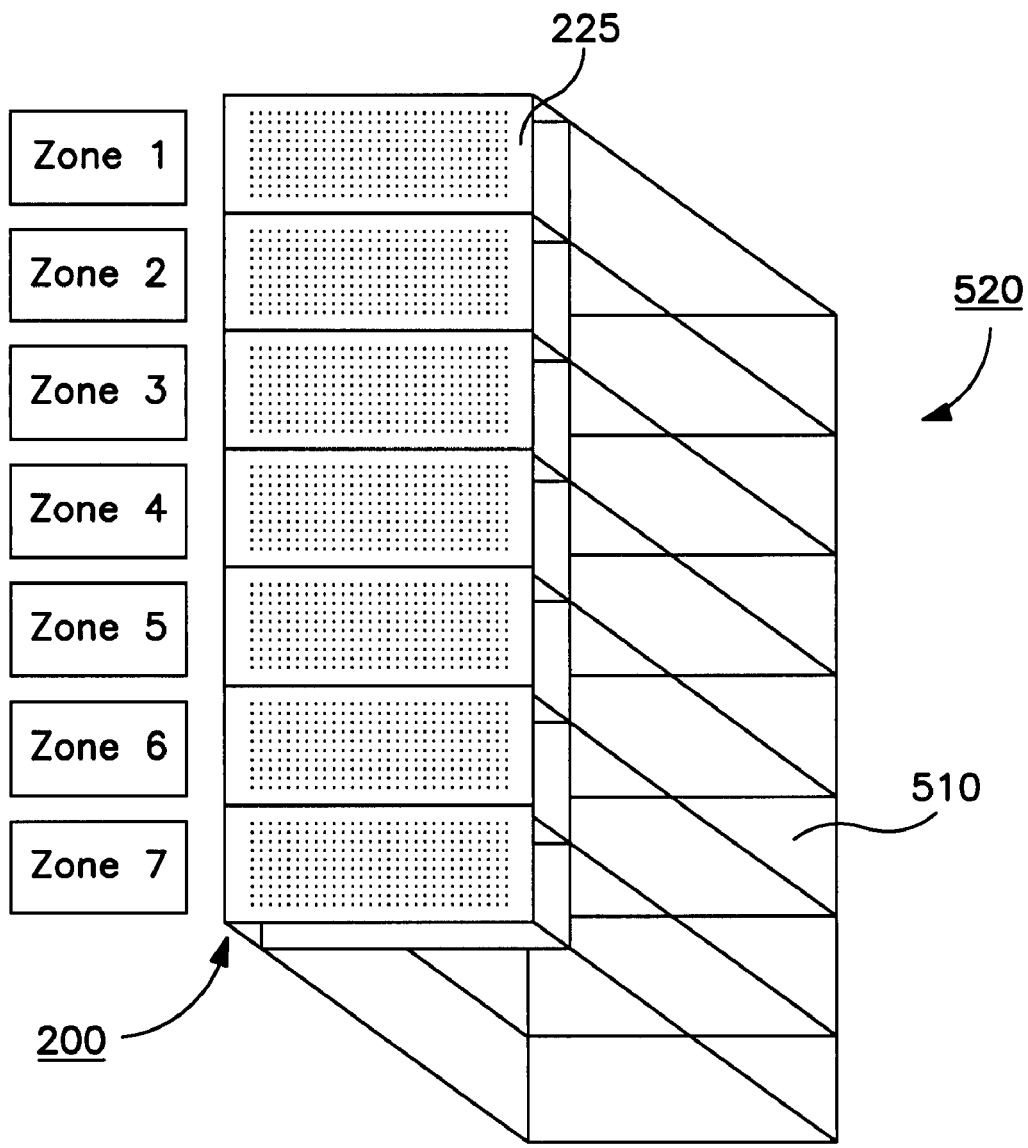
FIG. 3 illustrates a multi-zone microarray attached to manifold of individually controlled heater-cooler elements designed to differentially control the temperature of the individual zones.

In another embodiment, a single copy of the microarray is placed in or on an apparatus that differentially maintains the temperature of each of the 7 zones of the microarray at the temperature optimal, for example, for single base-pair mismatch discrimination by the probes arrayed in the zones. Many methods are available for controlling the temperature of the zones of the microarray in this way. For instance, a steady-state temperature gradient is established from one to the other of a metal block, and the microarray is fixed to the block in a manner to optimize temperature for each zone. In another instance, individual small electronic heater-cooler units are sandwiched together as a manifold as depicted in FIG. 3 and the microarray is fixed to the manifold. The units can be regulated individually to establish desired temperatures at specific zones of the chip.

In other embodiments, individual zones are more restricted in their range of Tm (nucleic acid duplex melting temperature), and thus include fewer oligonucleotide pools per zone. This would afford more precise discrimination of single base-pair mismatches between probes and sample oligonucleotides. In one such preferred embodiment, the zones comprise about 39 oligonucleotide pools (16 oligonucleotides per pool, as described above). A total of about 106 zones are formed in this embodiment, affording tight control of hybridization temperature and very high-resolution discrimination of, for example, single base pair mismatches. Temperature control units similar to those described above for the 7-zone embodiment are used with this embodiment, but are modified to control temperature gradient across the chip more finely and precisely.

In yet another embodiment, groups of pools of oligonucleotide probes are arrayed on separate chips, or sub-chips, wherein each sub-chip corresponds to one of the zones described in the embodiments recited above. Each sub-chip is separately heated to a different temperature, wherein the temperature is selected to provide optimal single base-pair mismatch discrimination between the oligonucleotide probes on the individual sub-chip and the sample oligonucleotides.

In one or more embodiments of the present invention, the number of oligonucleotide pools of the microarray may number at least about 1000 and no more than about 70,000 in number per microarray chip. The number of microarray spots used in a given application of the present invention is related, at least in a general way, to the number of different genes, or mRNA species, or other analyte nucleic acid molecules, or gene sequences present in the sample containing the sample sequence or sequences. Thus, for example, for a small genome, such as that from *E. coli*, containing about 5,000 genes, a smaller number of pools may be required than for complete analysis of the genome from an organism with a larger genetic complement, such as a human being with some 50,000 genes.

In some embodiments of this invention, labeled sample nucleic acid is applied directly to the microarrays of this invention. In preferred embodiments, primers that are complementary to at least a portion of the probes on the microarray are used to initiate synthesis of, for example, cDNA from sample mRNA.

The present invention also provides a set of primers, complementary in part to the spot probes, for the synthesis of nucleic acids. The primers have the form:

F-G wherein F and G are the same length as and complementary to the universal n-mer D, and variable x-mers C, respectively, of the array probes such that all possible $4^x$ permutations of F-G are represented in the set.

Figure 5:
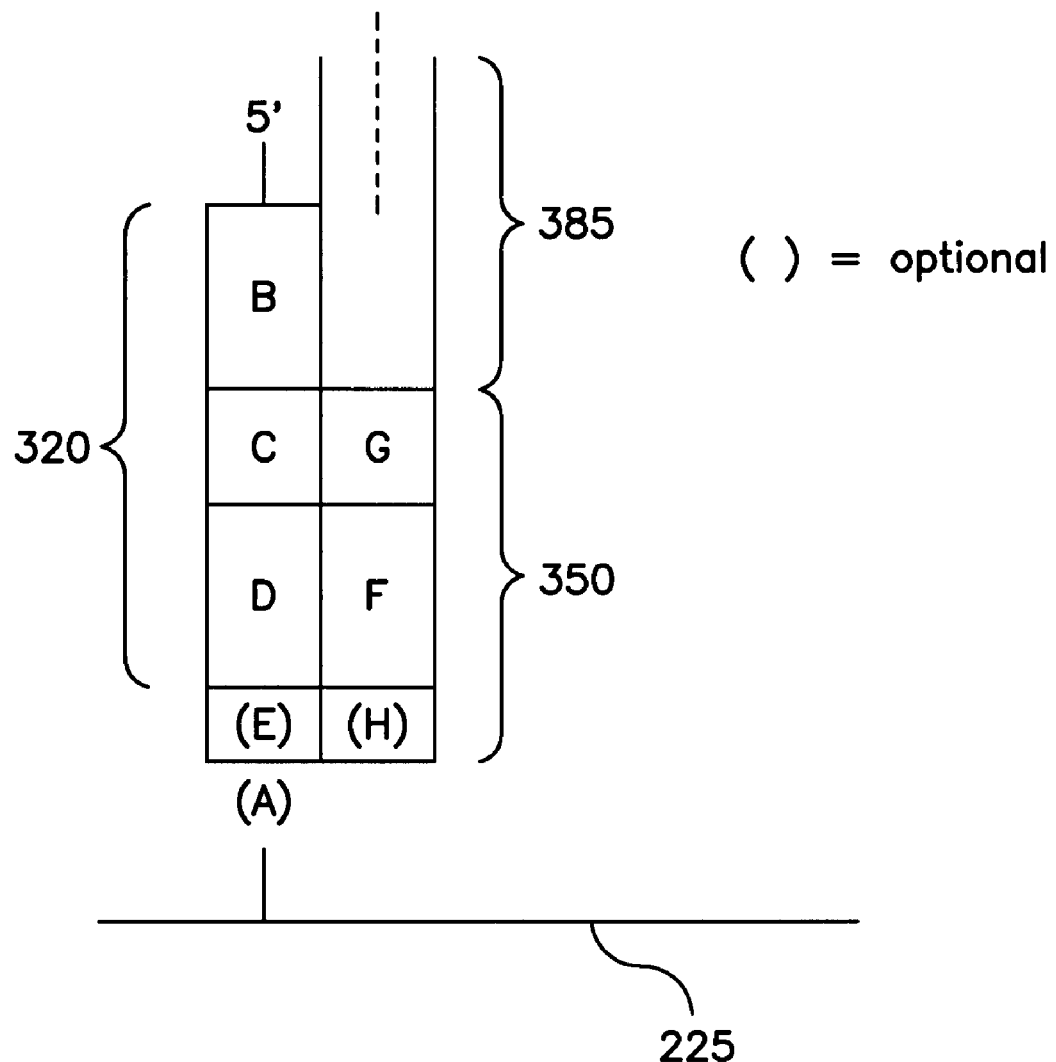
FIG. 5 illustrates one example of binding of cDNA to probes bound to a solid support.

In preferred embodiments, F and G are joined in the 5'- 3' direction when B, C, and D of the probes are joined in the 5'-3' direction. Such an arrangement facilitates hybridization of primers (and cDNA synthesized from them) to complementary probes (FIG. 5).

In another embodiment, the present invention relates to a set of primers wherein the primers further comprise a third portion, H, of about 1 to 5 nucleotides in length wherein, for any specific combinations of portions F and G, all possible combinations and permutations of the nucleotides will be equally represented in portion H. Portion H may be adjacent to either F or G. In one embodiment, portion H is included 5' to (adjacent to) portion F when the matching probes comprise optional portion E 3' to D. In this embodiment, H is complementary to optional portion E.

Using the primers, probes, and microarray of this invention, it is possible to utilize the described universal microarray for the determination of relative gene expression in two or more test mixtures. Generally, this method comprises a) providing a first set of a plurality of oligonucleotide primers having the form:

F-G wherein portion F is a universal n-mer comprising from about 5 to about 8 nucleotide bases and portion G is a variable x-mer comprising at least 1 nucleotide base such that all $4^x$ permutations of A, G, C, and T are represented said set of primers;

b) separately contacting each of the populations of mRNA derived from each of the 2 or more test mixtures to each of the members of said set of primers to generate $4^x$ primed mRNA populations for each sample;

c) segregating the primed mRNA populations into one or more subsets of mRNA populations;

d) separately synthesizing cDNA populations from each of the primed mRNA populations in each subset of mRNA populations by reverse transcription;

e) recovering each of said synthesized cDNA populations with said primers attached thereto to obtain one or more cDNA subsets corresponding to the subsets of the primed mRNA populations from which they were derived;

f) differentially labeling each member of a subset of cDNA populations.

g) providing a microarray for each subset of cDNA populations, such that portions C and D of the probes of said microarray are complementary to portions G and F, respectively, of the primer set used to synthesize the cDNA populations;

h) contacting one or more spots on the microarray with the differentially labeled members of a subset of cDNA populations such that each spot is contacted with all of the differentially labeled members of a subset of cDNA populations under conditions such that complementary cDNA and probe sequences hybridize;

i) repeating steps f-h for each subset of cDNA populations such that each subset of cDNA populations contacts a microarray not previously contacted with any other subset of cDNA populations;

j) detecting the signal generated from every spot on every array;

k) determining relative gene expression of the test mixtures by comparing the signal from a spot on one array to the corresponding spot on every other array wherein the probes on corresponding spots comprise the same unique z-mer or comparing the signal from different labels on s single spot on one microarray.

Figure 4:
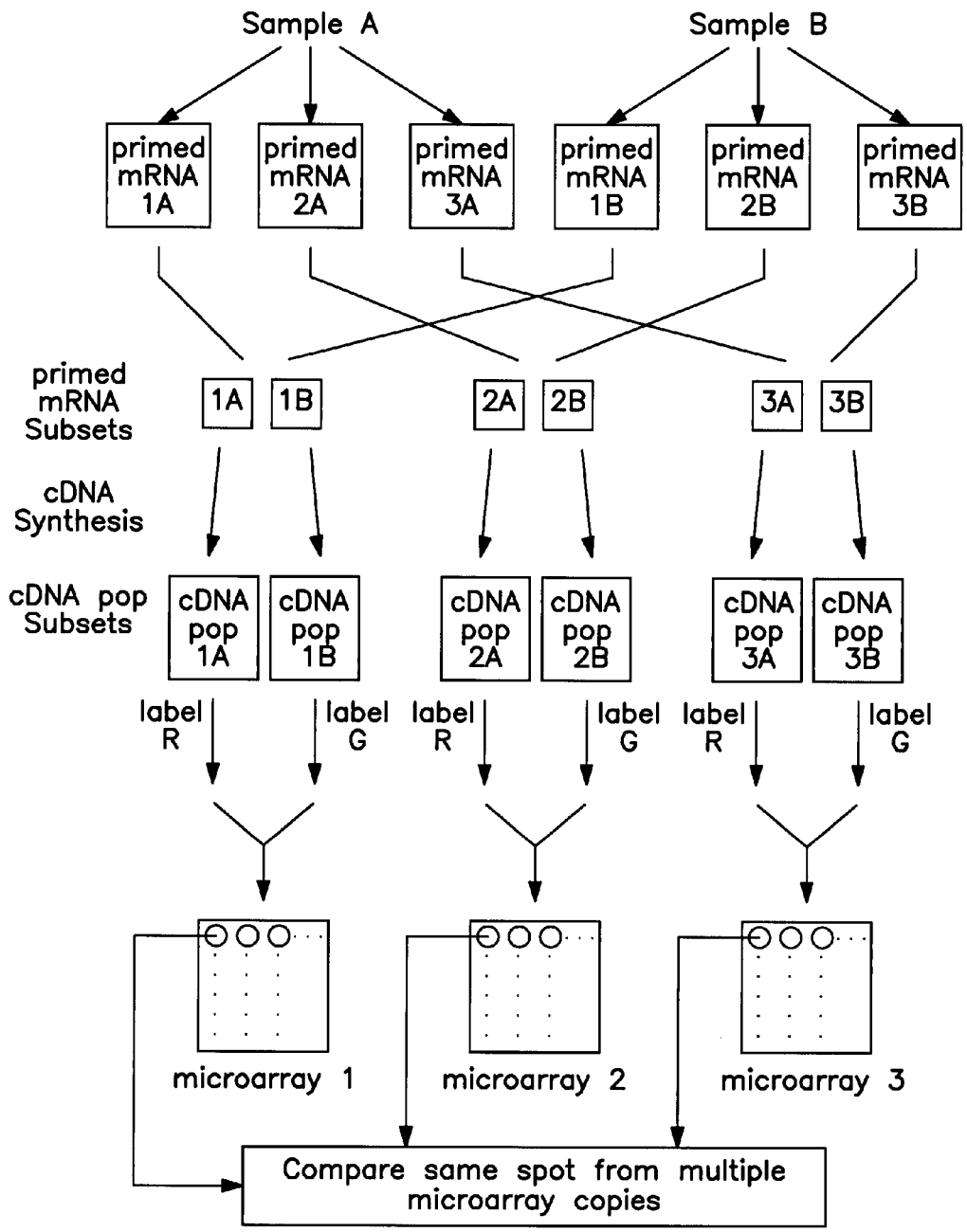
FIG. 4 illustrates a general method for determining relative gene expression in 2 or more test mixtures.

The method is illustrated generally in FIG. 4 and discussed in detail below.

The following is a specific example of how the microarray probes and the primers of this invention are designed based on genome size and average mRNA size. Based on the best determinations and estimates of current molecular biological knowledge, most species will have about 50,000 or fewer genes, and any tissue/cell type will express a fraction of these. In addition, the average mRNA size is assumed to be ~5000 bases so that the total number of bases in all expressed sequences would be around 250,000,000 bases.

Using these values, one can estimate that any given 6 base sequence will appear roughly once in every mRNA. Any one of 4 possible nucleotide bases (A, T, C, or G) can occur at any position within the 6-mer, resulting in $4^6$ =4096 possibilities. Since the average size of a mRNA is 5000 bases, we would expect, on average, 5000/4096 ≈1 occurrences in each mRNA. An estimate based on total bases of expressed sequence and a frequency of occurrence of any 6 base sequence yields a similar estimate: There should be 250,000,000/4096=61,000 occurrences of any given 6 base (or hexanucleotide) sequence in the expressed sequences of the genome. If these expressed sequences are distributed among 50,000 genes, then, on average, approximately 61,000/50,000 ≈1 occurrence of a given hexamer would occur in any given expressed gene. It is this universal hexamer that is used as the universal portion of the set of primers of this invention. Similar calculations can be employed to estimate the number of nucleotides needed in a universal x-mer to accommodate genomes of different estimated sizes. The size of the x-mer is selected such that on average there would be one occurrence of the x-mer in each expressed gene.

Figure 6:
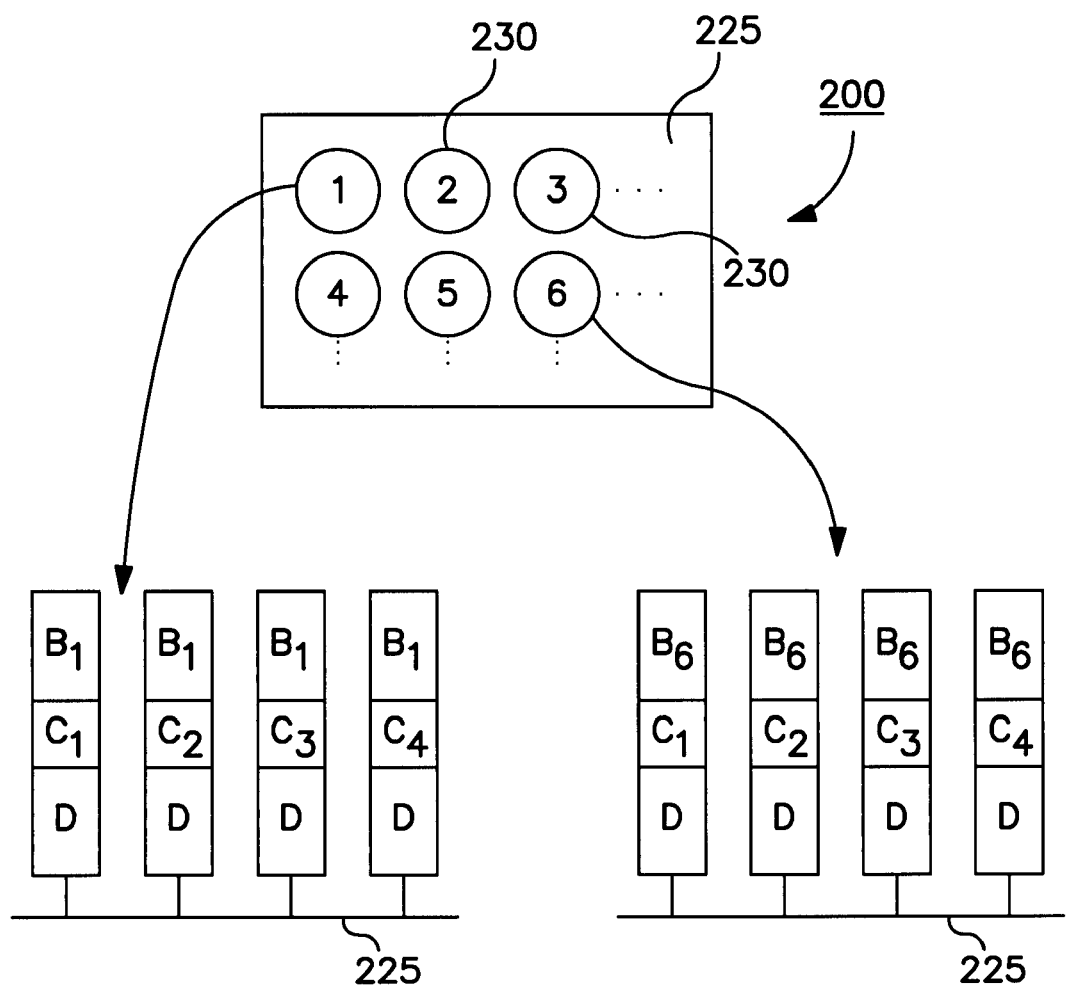
FIG. 6 illustrates the arrangement of oligonucleotide probes on the universal microarray.

The complement of this universal portion of the primer is also present in each probe such that cDNA synthesized using the primer will hybridize to the probe spots (FIG. 5). To discriminate among the different occurrences (~61,000) of a given hexamer in different mRNAs, the set of probes of the present invention utilizes all permutations (16) of two additional sequence elements (C) and all possible permutations of a 6-mer (4096) to yield a set of 65,536 ($4^8$) different probes. According to one embodiment of this invention, these 65,536 probes are arranged on the microarray into 4096 pools, or spots such that each probe pool contains oligonucleotides having identical 6-mers at the 3' end (D), referred to herein as the universal hexanucleotide or universal 6-mer, a variable central 2 base region of random sequence (C), and one of the 4096 permutations of the unique hexamer at the 5' end. Within the population of oligonucleotides present in a given pool, each base (A, T, G, or C) will be represented about equally at the two variable sites of C, so that the probe population of a particular pool (one of the 4096 pools on a given chip) will contain about equimolar amounts of each of 16 different sub-populations of oligonucleotides, which differ only at these two sites. The result is a set of 4096 pools, each comprising an approximately equimolar mixture of 16 different oligonucleotides, each of which is 14 bases in length. This arrangement is illustrated in FIG. 6 for a portion of pool oligonucleotides, where the microarray 200 comprises spots 230 on substrate 225.

Thus, in a given probe pool, for this embodiment of the invention, there are 16 kinds of 14-mers, all present in nearly equal amounts. These 16 different subpopulations of oligonucleotide probes in a given pool differ only in the identity of the particular nucleotide bases in variable portion C. Each probe pool differs from all other probe pools in the sequence of the unique hexamer. Since there are 4096 different possible unique hexamers, there are 4096 probe pools. In all probe pools, the universal hexamer is identical so that a given chip or microarray contains a single universal hexamer in all of the probes attached thereto and thus each pool differs from the other 4096 pools on the same chip only in the sequence of the unique hexamer (portion B).

In sum, for a non-limiting example using 14-mers as probes, a given probe pool will contain about equimolar amounts of 16 different 14-mers (i.e., 16 different oligonucleotides each of which is 14 nucleotide residues in length), 14-mers of the same pool differing only in the sequence of the second portion (the dimer representing nucleotides 7 and 8 of the 14-mer). In the third portion, D, representing the universal hexamer, this sequence is the same for all of the probes (14-mers) in a given pool and from pool to pool since each pool of the same microarray has the same 16 sub-populations. Thus, all of the 14-mers present in the 4096 pools of the microarray will have the same hexanucleotide sequence for the universal hexamer. The first portion, B, representing the unique hexamer, is a sequence of 6 nucleotides that is the same for all oligonucleotide probes (14-mers) in the same pool but differs between the oligonucleotide probes (14-mers) from one pool to another, giving a unique 6-mer (portion 1) for each of the different 4096 pools on the same chip.

The result is that this set of probe pools spotted upon a single chip contains an oligonucleotide capable of hybridizing to any occurrence of the universal hexamer that appears within the genome as represented by a mRNA or cDNA sequence derived from said genome. The 14 base sequence is long enough to provide stable hybridization so that the presence of the universal hexamer (portion 3) facilitates binding of all of the different cDNAs encoded by the fully expressed mRNA complement in a given sample, thereby representing the expression of all active genes present in a cell source.

The 8 (eight) bases present in addition to the universal 6-mer allows discrimination between all possible occurrences of the hexanucleotide (where a cell might contain 50,000 active genes producing 50,000 mRNAs and the 8-mer provides for $4^8$ or about 65,000 unique octanucleotide sequences) attached to the universal hexamer present on a given chip. Because statistical analysis indicates that the vast majority of mRNAs present in a cell will contain the complement of the universal hexamer some place in their sequence, a cDNA will be synthesized from virtually every mRNA in the population using one of the 16 octamer primers used in this invention, each of which contains the complement of the universal hexamer. Because each complementary hexamer will be followed by an octamer (which must be complementary to one of the probe sequences on the chip, since all possible octamers are represented on the chip), all the cDNAs from a sample will bind somewhere on the chip and thus be detectable.

One such set of probes (i.e., all of the probes on a single microarray) should detect the cDNAs encoded by virtually every mRNA expressed in any given cell type. Thus, an assay employing one set of such probes is useful for detecting most mRNAs expressed. To decrease the chance of not detecting all expressed mRNAs in a given sample, multiple sets of probes and primers, each set using a different universal x-mer, can be employed to assay a given sample. The number of additional sets of probes and primers to be used will depend upon the size of the genome and the detection accuracy that is desired. Typically, the use of 2 or 3 sets will be sufficient. For instance, if a single array based on a single universal hexamer will detect 95% of mRNAs, a second array will detect 95% of the remaining 5% yielding a total coverage of 99.75%, and a third will detect 95% of the remaining 0.25%, yielding a total coverage of 99.9875%. Based on this analysis, for a mRNA population of 50,000, screening with a single universal hexamer array will miss 2,500 mRNAs, screening with two arrays will miss 125 mRNAs and screening with three arrays will miss 6.25 mRNAs.

In order to increase the stability of hybridization between probes and sample sequences, it may be necessary, in certain cases, to add a fourth portion, E, to the probe structure. Accordingly, in certain embodiments, additional (Portion E) nucleotides will be added to the probe adjacent to the unique portion (portion B) or the universal portion B (portion D). In a given probe population, all four (A, G, C, and T) nucleotides are incorporated at each site within the fourth portion, resulting in a probe population in which all possible sequences of the fourth portion are linked to all possible combinations and permutations of sequences of portions B, C, and D.

The universal microarray of this invention provides qualitative, semi quantitative or quantitative evaluation or profiles of all of the mRNAs expressed in a given cell type or tissue, as long as that population contains fewer than 65,536 mRNAs in the preferred 14-mer embodiment of the microarray, and as long as that population is less than the corresponding upper limit relevant to embodiments in which the oligonucleotide probes are longer or shorter in length. Such a system should be capable of comparing the expression profiles of the same tissue/cell type under many different conditions, or of different tissue or cell types, and can also be used for other purposes.

In order to utilize the microarray of the present invention, cDNAs are first synthesized in solution, in the preferred embodiment, from octamer primers comprising sequence portions F and G, as described above.

Because the primers differ only at the dinucleotide (complementary to the second or middle portion of the above-described probe) of portion G, there will be 16 different primers. Thus, the 5' 6-mer, F, of each primer is the same in all 16 primers, and presents the complement of the universal 3' 6-mer, D, of the probe set. The two 3'-most bases of each primer, portion G, differ for each of the 16 primers. Each of the 16 primers will contain one of the 16 possible 2-mers at this location. The structures for this set of primers are represented in Table 1. These primers bind to the vast majority of the mRNAs in a given genomic sample because (as stated previously) the universal primer should be present, on average, at least once in each of the mRNA molecules expressed in a given cell.

TABLE 1

| Primer Number | Bases #1–#6 | Base #7 (X') | Base #8 (Y') |
|---|---|---|---|
| 1 | Complement to Universal Hexamer | A | A |
| 2 | Comp. Univ. Hex. | A | C |
| 3 | Comp. Univ. Hex. | A | G |
| 4 | Comp. Univ. Hex. | A | T |
| 5 | Comp. Univ. Hex. | C | A |
| 6 | Comp. Univ. Hex. | C | C |
| 7 | Comp. Univ. Hex. | C | G |
| 8 | Comp. Univ. Hex. | C | T |
| 9 | Comp. Univ. Hex. | G | A |
| 10 | Comp. Univ. Hex. | G | C |
| 11 | Comp. Univ. Hex. | G | G |
| 12 | Comp. Univ. Hex. | G | T |
| 13 | Comp. Univ. Hex. | T | A |
| 14 | Comp. Univ. Hex. | T | C |
| 15 | Comp. Univ. Hex. | T | G |
| 16 | Comp. Univ. Hex. | T | T |

In sum, every, or nearly every, mRNA molecule in a given test mixture should be bound by one of the 8-mer primers (16 different ones in all), the former then acting as templates for cDNA formation starting at the complement of the octamer primers. After completion, the cDNAs are resolved from the reaction mixture and then probed with the 14-mer probes attached to the microarray of the invention under appropriate hybridization conditions (FIG. 5). In this example, probe 320 is attached to the microarray substrate 225 through linker A. Complementary primer 350, and any labeled synthesized cDNA 385 extended from that primer.

Of course, there will be many more than 16 different cDNAs formed as a result of this procedure since one of the 16 8-mer primers will bind to each one of the up-to 50,000 mRNAs present in the sample. The universal hexamer serves the function of binding the octamer primer to some position within each mRNA molecule present in the sample (i.e., it will bind somewhere in each of the different mRNA molecules of the genetic complement of the cell used as source of the sample). Each of the 16 8-mer primers contains of the universal hexamer plus one of the 16 possible 2-mers of A, G, C and T. One of these 16 primers will bind to any possible occurrence of the universal hexamer. Since, on average, one such occurrence will be present in each mRNA of the mRNA population isolated from the cells or tissue of interest, this set of primers should prime cDNA synthesis from all, or almost all, mRNAs in that population.

To increase stability of primer-template interactions, an additional segment or portion of 1 to about 5 nucleotides can be incorporated into the primer. In preferred embodiments, portion H is incorporated into the primer at the 5' end, adjacent to portion D. All 4 nucleotides are incorporated at these sites such that all possible permutation of A, G, C and T are present in the primer set.

In the preferred embodiment of this invention, 16 separate cDNA syntheses are performed for each mRNA preparation, one with each of the octamer primers described above. Each of the cDNA preparations is then probed with the microarray under appropriate hybridization conditions, wherein each spot contains 16 different 14-mer probes (each differing in the XY-middle portion C). Probes bound in each spot differing from all of the other pools or spots by the unique hexamer sequence. The universal hexamer is the same for each probe in each of the pools and through all of the pools spotted on the chip (for example, all 4096). cDNA that is complementary to all of the portions of a given probe will hybridize to that probe (FIG. 5).

In accordance with the foregoing, each of the cDNA syntheses will be carried out under identical conditions, except that each of the 16 reactions will contain a different one of the 16 octamer primers. Different dye-linked dNTPs will also be present in the different reactions. In addition, the remainder of the procedures disclosed herein may be somewhat less than optimal if a mRNA of interest contains a sequence complementary to this octamer but said sequence happens to lie at or very near the 5'-end, thus possibly interfering with adequate synthesis of a cDNA. By making use of microarrays and sets of primers that are based on several different universal hexamers, it is possible to greatly increase the probability that all mRNAs in a given sample will be detected by at least one of the multiple microarrays.

Expression profiling experiments are useful in comparing levels of expression of an mRNA under at least two sets of biological conditions. Results identify mRNAs (cDNAs) that are significantly increased or decreased in amount between the different conditions.

While the sample oligonucleotides used with the probes and primers of the present invention can be either DNA or RNA in nature, it should be borne in mind that not all hybrids resulting therefrom are equally stable. The stability of the resulting duplexes is generally RNA:RNA as the most stable and DNA:DNA the least stable, with DNA:RNA hybrids being somewhere in between, where such duplexes have been observed in solution. It is expected that such relative stabilities will hold up when one of the strands is attached to a solid support, as disclosed herein.

It should be kept in mind that the probes preferred in practicing the present invention are approximately 14-mers with a dinucleotide wobble sequence portion and that part of the utility of the invention is the ability of the middle portion of the probe to prevent hybridization of the universal and unique hexanucleotide segments when there is a mismatch in the middle portion. Thus, such shorter sequences, as the 14-mers of the invention, are highly useful in discriminating among mismatched segments. However, stability of the resulting duplexes (between probe and sample sequence) will not be optimal in all cases.

This problem can be minimized by selecting universal hexamers of higher GC content. However, duplex stability will still be low at array spots where the unique hexamer is high in A-T content. By using microarrays and primer sets that are based on several different universal hexamers, reasonably stable duplexes between probes and sample sequences should be obtained with at least one of the universal hexamer arrays for the vast majority of mRNAs.

This problem can also be solved by designing the microarray in zones, each of which comprises pools of oligonucleotide probes of similar melting temperature spotted in close proximity on the microarray. As described above, multiple copies of such a microarray, or separate sub-chips can be hybridized under conditions optimal for single base pair mismatch discrimination by the pools of oligonucleotide probes of a given sub-chip.

In addition, depending on the source of test mixtures and the conditions under which procedures of the inventions are to be carried out, it may be necessary to seek other approaches to bolster or modulate duplex stability. For instance, procedures are well known in the art for using various nucleotide analogues for the inducement of greater duplex stability while maintaining mismatch discrimination (i.e., the ability of a probe sequence to avoid hybridization with a sample sequence having a different nucleotide sequence, especially where said difference is limited to a single nucleotide). Such mismatch discrimination will generally be reflected in the observed signal ratio between a sequence wherein the probe and sample sequence are matched exactly and one wherein there is at least one mismatch. In general, the shorter the probe, the better the mismatch discrimination but the less the stability of the resulting duplexes. Such problems of stability may arise where the sequences of the 14-mers of the invention contain a longer than acceptable stretch of adenine or thymine residues (uracil for mRNA) since AT or AU pairs form only 2 hydrogen bonds and are thus less stable that GC pairs that form 3 hydrogen bonds.

Probes useful in practicing the present invention are selected to yield an advantageous combination of excellent mismatch discrimination and good duplex stability. The 14-mer probes preferred for the practice of this invention provide this balance of properties. Methods of increasing stability, where this is necessary, are well known in the art. For example, replacing an adenine base by 2,6-diaminopurine will usually increase duplex stability while maintaining mismatch discrimination. However, one advantage of the present invention is that it allows for both sensitive mismatch discrimination and good duplex stability without the need to resort to use of nucleotide analogs to achieve the same result.

In accordance with the present invention, the solid supports disclosed herein may have attached to them a spacer or linker molecule for joining of the probe oligonucleotides to the substrate, depicted as segment A in FIG. 5. Such spacer will commonly attach to the 3'-OH end of the probe or to a linker structure attached thereto to facilitate chemical reactions needed to form the array. The oligonucleotide probes (i.e., the 14-mers disclosed herein) may be synthesized in solution and then attached to said solid support or may be synthesized stepwise on said support. The method of preparation of such array in no way limits the breadth or utility of the invention.

The primary use of the microarrays of the present invention is in gene expression profiling, although they can also be used in diagnostic procedures designed to detect the presence of a mutation in a specific sample sequence or a change in gene expression profile characteristic of a given disease state. The objective of gene expression profiling is to determine the relative abundance of mRNA sequences in a population, thereby measuring relative expression of one or several genes of a genome. For example, where one is to compare gene expression in a cancerous cell with that of an otherwise normal cell. The presence or absence of such mutations is commonly detected by the ability of a given molecular species, such as a given mRNA or cDNA, to bind to a probe sequence. Relative gene expression is indicated by the relative degree of signal intensity resulting from binding to probe sequences for molecules derived from the same or different genomes.

The probes useful in practicing the present invention will commonly be laid down in matrix form as definite rows and columns but such an arrangement is not absolutely essential to practicing the invention and other arrangements are specifically contemplated. The only requirement is that the spatial location of each group of probes (as defined by the unique z-mer, B) in a given array is known, or can be readily determined. For example, probes may be attached to a plurality of microspheres, wherein each microsphere represents a 'spot' on an array. The microspheres are readily identifiable, and thus the 'location' of each group of probes is determinable.

The probes are oligonucleotides or oligonucleotide analogues which are capable of hybridizing with a sample nucleic acid sequence by complementary base-pairing. Complementary base pairing includes sequence-specific base pairing, which comprises, e.g., Watson-Crick base pairing or other forms of base pairing such as Hoogsteen base pairing.

In accordance with the foregoing, use of the apparatus and processes disclosed herein depends on a reliable detection strategy, which in turn relies on a labeling strategy. The labeling strategy used is designed to enable the operator to distinguish between all the cDNA populations generated from the separately primed mRNAs. In the example discussed below, the number of distinct cDNAs is 32 (for example, 16 cDNA populations synthesized from mRNA preparation #1 and 16 from mRNA preparation #2) if two different mRNA populations are utilized, that could hybridize to any given spot on the microarray.

This is achieved by (1) using different dyes to label cDNAs derived from different primers, (2) using different dyes to distinguish between cDNAs derived from different mRNA populations and (3) hybridizing different subsets of the 16 cDNA populations to different copies of the universal microarray.

The labeling scheme selected depends not only on the dyes that are selected but also on the capabilities of the scanner used to analyze the array. For example, in the simplest case, if a scanner is used that is capable of distinguishing clearly between 32 different dyes in a spot, then the scheme for cDNA synthesis presented in Table #2 can be used. Commercially available scanners can, for example, differentiate from 2–8 dyes. One example of a 4 color scanner is the Array Worx$^{e\text{TM}}$ from Applied Precision which can differentiate, for example, between Cy3, Cy5, Alexa 350 and Alexa 488 and provides the flexibility of choosing among 89 fluorescent dyes.

The labeling scheme presented in Table #2 is used, for example, to compare the levels of expression of specific mRNAs within two mRNA populations that were isolated from the same tissue or cell type but that were subjected to different biological conditions. Sixteen dyes would be used to label the cDNAs derived from one mRNA population, and another sixteen dyes would be used to label the cDNAs derived from the second mRNA population. In a preferred operation of the assay, equimolar amounts (based on fluorescence) of each cDNA product would be pooled and hybridized to a universal microarray. Alternatively, non-equimolar amounts of cDNA may be used if the concentrations of cDNA in each product is known and the differences in concentration are taken into account during analysis of relative amounts. After processing, the array is scanned for all 32 dyes. Assuming that the hybridization signal due to any given dye at any given microarray spot is due to a single mRNA (a reasonable assumption based upon the discussion above), comparing the intensity of the signal for dye #1 with that for dye #17, for instance, at a specific spot will indicate whether expression of that particular mRNA changes or is different in the two biological conditions of interest. An analogous comparison would be made for the dyes corresponding to each primer.

TABLE 2

| Oligo Sequence | cDNA from mRNA Pop. #1 Dye Site #7 | cDNA from mRNA Pop. #2 Dye Site #8 |
| --- | --- | --- |
| Complement to Univ 6-mer AA | 1 | 17 |
| Compl. Univ 6-mer AC | 2 | 18 |
| Compl. Univ 6-mer AG | 3 | 19 |
| Compl. Univ 6-mer AT | 4 | 20 |
| Compl. Univ 6-mer CA | 5 | 21 |
| Compl. Univ 6-mer CC | 6 | 22 |
| Compl. Univ 6-mer CG | 7 | 23 |
| Compl. Univ 6-mer CT | 8 | 24 |
| Compl. Univ 6-mer GA | 9 | 25 |
| Compl. Univ 6-mer GC | 10 | 26 |
| Compl. Univ 6-mer GG | 11 | 27 |
| Compl. Univ 6-mer GT | 12 | 28 |
| Compl. Univ 6-mer TA | 13 | 29 |
| Compl. Univ 6-mer TC | 14 | 30 |
| Compl. Univ 6-mer TG | 15 | 31 |
| Compl. Univ 6-mer TT | 16 | 32 |

Another labeling scheme would use two dyes. In this case, the cDNAs derived from the 16 different primers are each hybridized to different arrays. By way of a non-limiting example, wherein two mRNA populations are to be compared, one stars with two mRNA preparations derived from the same cell type grown under two different conditions (condition #1 and #2 resulting in mRNAs #1 and #2, respectively). A cDNA preparation is synthesized from the mRNA population extracted from cells exposed to condition #1 using primer AA and the dye Cy3. A CDNA preparation is synthesized from mRNA population #2 using the same primer and the dye Cy5. After synthesis, the cDNAs are isolated from other reaction components, and preferably equimolar amounts of these two cDNA preparations are combined and hybridized to the same copy of the universal microarray. Similarly, cDNAs corresponding to mRNAs #1 and #2 would be synthesized separately using the dyes Cy3 and Cy5, respectively and primers AC, AG, AT, CA, CC, or CG, etc. Each pair of cDNAs would be hybridized to a different copy of the same universal microarray. Thus, for a complete analysis, 16 copies of the universal microarray would be used in this case. Depending on the performance of the scanner, more dyes (e.g. 4 or 8) can be used allowing increasing numbers of cDNA preparations (derived using different copies of the same primers) to be hybridized to the same copy of the universal microarray, thereby reducing the number of arrays required for a given experiment.

Examples of existing commercial scanning equipment are as follows: HP GeneArray® Scanner; Affymetrix® 418 Array Scanner, Affymetrix® 428 Array Scanner; Packard Bioscience BioChip Technologies LCC: ScanArray™ Express, ScanArray™ Express HT, ScanArray™ Lite, ScanArray 4000 and ScanArray 5000; Genometrix Bioscanner™; Applied Precision: ArrayWorx.

Figure 7:
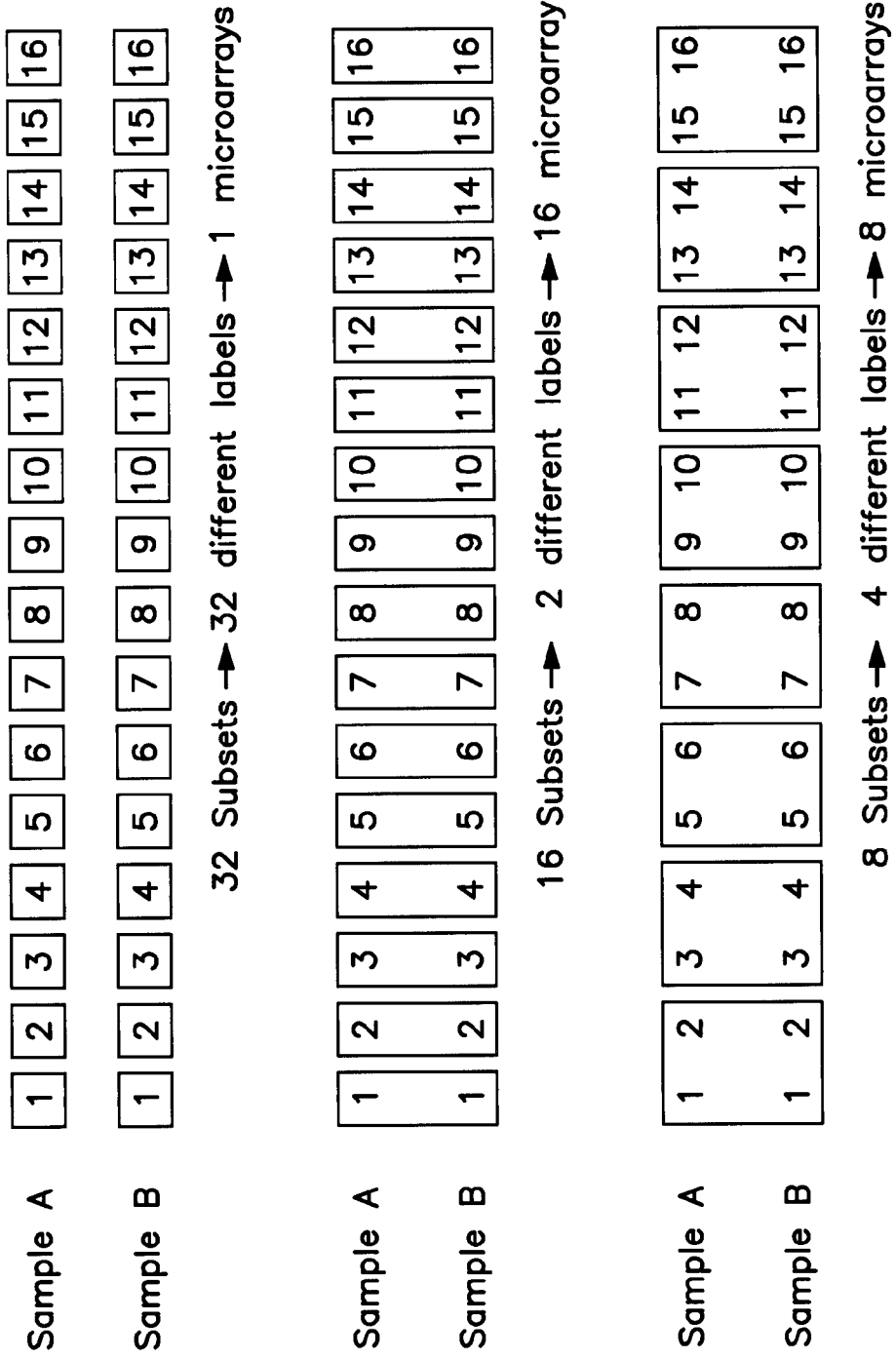
FIG. 7 illustrates three examples of cDNA labeling and pooling strategies.

More generally, cDNA populations are divided into one or more cDNA population subsets comprising one or more cDNA populations. Each member of a cDNA population subset is differentially labeled such that each member of a subset can be distinguished from any other member of the subset. Differential labels can include fluorescent, electroluminescent, chemiluminescent, and bioluminescent dyes, radiolabels, microparticles, electron spin labels, and other labels known in the art. Some suitable labels are described in U.S. Pat. No. 6,344,316, which is incorporated herein in its entirety to the extent not inconsistent herewith. In addition, different types of labels can be employed in a given assay. For example, labeling with 2 dyes can be combined with labeling using 2 different sizes of microparticles. This general strategy is outlined in FIG. 7.

After labeling, members of the same subset are contacted with each spot on a microarray containing probes that are complementary, in part, to the primers used to synthesize the cDNA, under conditions that allow hybridization of the cDNA to the probes. Each remaining subset is contacted to its own array until all cDNA populations have been interrogated. Because the cDNA populations are differentially labeled, it is then possible to determine the sequence of at least part of the cDNA based on the spot on the microarray to which it is bound. The cDNA, and ultimately the mRNA from which it was derived, may then be sequenced and identified using a variety of techniques known in the art.

This general scheme for labeling subsets is illustrated for the example of 16 primers used with two test mixtures (32 separate cDNA populations).

Methods of labeling nucleic acids are well known in the art. In the example described above, labeling may occur during synthesis, or after synthesis of cDNA from the sample mRNA. Labeling may also be direct or indirect. Direct labeling comprises incorporation of the label directly onto the sample nucleic acid. Indirect labeling comprises first attaching a chemical moiety, binding pair, or functional group to the nucleic acid then attaching a label via the moiety, binding pair, or functional group. One example of indirect labeling is the use of the avidin-biotin interaction to, for example, first biotinylate the nucleic acid, then add an avidinated label. Indirect labeling may also occur during synthesis, after synthesis, or after hybridization of the sample nucleic acid to the microarray.

In one strategy for labeling the sample nucleic acids during synthesis, the labeling reactions contain, for example, an enzyme, such as reverse transcriptase for cDNA synthesis, a reaction buffer, $MgCl_2$, mRNA, primer, and two kinds of each dNTP: (1) unmodified dNTP, and (2) labeled dNTP. If desired, a dideoxy derivative of one of the four dNTPs is present in an amount adjusted to terminate transcripts after the addition of about 50 to 100 nucleotide units. The relative amounts of each dNTP form are adjusted empirically to give the optimal level of labeling and termination. Alternatively, the terminating dNTP is labeled such that the sample nucleic acid is labeled at its terminus.

A diversity of hybridization conditions may be used in the present invention, according to methods known to those skilled in the art. These may be of low, medium or high stringency. Those of ordinary skill in the art would be capable of choosing stringency conditions, for example, to balance the desired level of binding with an acceptable degree of mismatch discrimination. Examples are to be found in Sambrook, et al., Molecular Cloning: A Laboratory Manual, Third Edition, Cold Spring Harbor, N.Y. (2000), and Short Protocols in Molecular Biology, ed. Ausubel, et al., both incorporated here by reference. The hybridization conditions may also vary when either probe or sample molecules contain modified bases, or when the backbone of the polymer is modified, as in the case of PNA, where the backbone structure is non-ionic, as known in the art. In addition, cross-linking agents may be used, after hybrids are formed, to form cross links between probe and sample sequence, thereby stabilizing that interaction, also as known in the art. In a preferred embodiment, hybridization conditions and probe nucleotide modifications will be designed to optimize discrimination between sample sequences differing by only a single base pair. For instance, strategies such as those described by Nguyen, et al., *Nucleic Acids Res.*

27:1492–1498 (1999) and Matray, et al., *Nucleosides Nucleotides Nucleic Acids* 19:1553–1567 (2000), both incorporated here by reference, will be used to achieve these objectives. Perfect hybrids of oligonucleotides 11 to 20 nucleotides in length can be distinguished from hybrids containing a single internal mismatch [Wallace et al., Nucl. Acids Res. 6: 3543 (1979)]. Discrimination is based on the difference in the amount of hybrid formed in the hybridization step and/or the amount remaining after the washing steps [Ikuta et al., Nucl. Acids Res. 15: 797 (1987); Thein and Wallace, in Human Genetic Diseases: A Practical Approach, ed. by J. Davies, IRL Press Ltd., Oxford, pp. 33–50 (1986)]. Wood et al., [Proc. Natl. Acad. Sci. 82: 1585 (1985)] describe conditions for hybridization of 11 to 20 base long oligonucleotides using 3M tetramethyl ammonium chloride wherein the melting point of the hybrid depends only on the length of the oligonucleotide probe, regardless of its GC content. However, eleven base long oligonucleotides are the shortest ones that can be hybridized successfully using known hybridization conditions.

In separate embodiments, this process contemplates each said mRNA population being derived from a different tissue or cell type, such as where each such type has been maintained under different physical and/or chemical conditions or where one population is derived from cancerous cells, or some other pathological state, and the other population from otherwise normal cells of the same cell or tissue type. Commonly, each such mRNA population will represent the entire complement of mRNAs from the given cell or tissue type.

Once synthesis of the cDNA populations is completed for each mRNA and the cDNAs are isolated from other reaction components, cDNAs are combined and hybridization to universal microarrays carried out as follows, keeping in mind that different strategies for pooling cDNAs are available depending on how the cDNAs have been labeled and depending on the capability of the scanner. Increased capability of the scanner will increase the number of dyes that can be used and reduce the number of copies of the microarray that will be needed for a complete analysis. The strategy used for two labeling schemes are described above.

In another embodiment, this invention provides kits for the determination of gene expression and relative gene expression. The kits include, but are not limited to one or more universal microarrays of this invention. The kits can also include a label or labels for labeling one or more sample nucleic acid specimens. In addition, the kits may contain primers that are complementary, or matched, to the probes of the universal microarray or microarrays, as described herein. One of skill in the art will appreciate that the kits may include any other of the various reagents, buffers, dNTPs, enzymes, labels, and the like useful for performing the nucleic acid syntheses, and hybridizations described herein as well as instructions for using the contents of the kits.

In forming the microarrays useful in the present invention, the oligonucleotides are typically attached to the chip via the 3'OH group. Chemical techniques for doing so are well known in the art and some are disclosed herein. These methods might include photo-removable protecting groups and the like, with the general approaches being similar to those used in oligonucleotide synthesis itself. Groups typically available on the chip for forming the appropriate bonds include esters, ethers, phosphate esters and carbamates. Other methods are well known. See for example, the methods described in U.S. Pat. No. 6,156,501 and references contained therein and the methods in the following articles: Zammatteo, N, et al., Anal. Biochem. Apr 10,2000 280(1): 143–50; Joos, B, et al., Anal. Biochem. Apr 5,1997 :247(1): 96–101; Cohen, G., et al., Nucleic Acids Res. 1997 Feb 15;25(4):911–2; Beaucage, S. L., Curr. Med. Chem. 8:1213–1244, 2001; Ghosh, S. S., et al., (1987), Nucleic Acids Res. 15:5353–5372; Beier, M., Hoheisel, J. D. (1999), Nucleic Acids Res. 27:1970–1977; Gingeras, T.R., et al., (1987), Nucleic Acids Res. 15:5373–5390; Joos, B., et al., (1997), Anal. Biochem. 247: 96–101; Kumar, A., et al., (2000) Nucleic Acids Res. 28:E71; Lindroos, K., et al., (2001), Nucleic Acids Res. 29:e69; Lund, V., et al., (1988) Nucleic Acids Res. 16:10861–10880; Maskos, U., et al., (1992), Nucleic Acids Res. 20:1679–1684; O'Donnell, M. J., et al., (1997) Anal, Chem. 69:2438–2443; Proudnikov, D., et al., (1998) Anal. Biochem. 259:34–41; Rasmussen, S. R., et al., (1991) Anal. Biochem. 198:138–142; Rehman, F. N., et al., (1999) Nucleic Acids Res. 27:649–655; Rogers, Y. H., et al., (1999) Anal. Biochem. 266:23–30; Bahl, C., et al., (1993), U.S. Pat. No. 5,215,882; Bradley, A., et al., (1998), U.S. Pat. No. 6,048,695; Dattagupta, N. (1989), U.S. Pat. No. 4,818,681.

Attachment of oligonucleotides disclosed herein to useful solid state supports for forming the microarray system of the invention can be through means of any kind of molecular species, such as some type of polymer, biological or otherwise, that serves to attach said oligonucleotide to a solid support. Solid-state substrates useful in the methods of the invention can include any solid material to which oligonucleotides or modified oligonucleotides can be coupled. This includes materials such as acrylamide, cellulose, nitrocellulose, glass, polystyrene, vinyl acetate, polypropylene, polymethacrylate, polyethylene, polyethylene oxide, polysilicates, polycarbonates, teflon, fluorocarbons, nylon, silicon rubber, polyanhydrides, polyglycolic acid, polylactic acid, polyorthoesters, polypropylfumerate, collagen, glycosaminoglycans, metals, and polyamino acids. Solid-state substrates can have any useful form including but not limited to thin films, membranes, and microspheres.

Methods for immobilization of oligonucleotides to solid-state substrates are well established. Oligonucleotides can be coupled to substrates using established coupling methods. For example, suitable attachment methods are described by Pease et al., *Proc. Natl. Acad. Sci. USA* 91(11):5022–5026 (1994). A preferred method of attaching oligonucleotides to solid-state substrates is described by Guo et al., *Nucleic Acids Res.* 22:5456–5465 (1994).

Oligonucleotides useful in forming the microarrays of the present invention can be synthesized using established oligonucleotide synthesis methods to afford any desired sequence of nucleotides. Methods of synthesizing oligonucleotides are well known in the art. Such methods can range from standard enzymatic digestion followed by nucleotide fragment isolation (see for example, Sambrook, et al., Molecular Cloning: A Laboratory Manual, Third Edition, Cold Spring Harbor, N.Y., (2000), Wu et al, *Methods in Gene Biotechnology* (CRC Press, New York, N.Y., 1997), and *Recombinant Gene Expression Protocols*, in *Methods in Molecular Biology*, Vol. 62, (Tuan, ed., Humana Press, Totowa, N.J., 1997), the disclosures of which are hereby incorporated by reference) to purely synthetic methods, for example, by the cyanoethyl phosphoramidite method using a Milligen or Beckman System 1 Plus DNA synthesizer (for example, Model 8700 automated synthesizer of Milligen-Biosearch, Burlington, Mass. or ABI Model 380B). Synthetic methods useful for making oligonucleotides are also described by Ikuta et al., *Ann. Rev. Biochem.* 53:323–356 (1984), (phosphotriester and phosphite-triester methods), and Narang et al. *Methods Enzymol.*, 65:610–620 (1980), (phosphotriester method). Protein nucleic acid molecules can be made using known methods such as those described by Nielsen et al., *Bioconjug. Chem.* 5:3–7 (1994). Synthetic methods useful in synthesizing oligonucleotides containing reactive groups useful in attaching said oligonucleotides to solid substrates are well know in the art. See, for example, Bischoff, R., et al., (1987) Anal. Biochem. 164(2): 336–344; Connolly, B. A. et al., (1985) Nucleic Acids Res. 13:4485–4502; Farmar, J. G. et al., (1991) Biotechniques 11:588–589; Jablonski, E., et al., (1986) Nucleic Acids Res. 14:6115–6128; Li, P., et al., (1987), Nucleic Acids Res. 15:5275–5287; Nelson, P. S., et al., (1989) Nucleic Acids Res., 17:7179–7186; Nelson, P. S., et al., (1992) Nucleic Acids Res. 20:6253–6259; Sinha N. D. et al., Nucleic Acids Res. 16:2659–2669; Sproat, B. S., et al., (1987) Nucleic Acids Res. 15:4837–4848; Telser, J., et al., (1989) J. Am. Chem. Soc. 111 :6966–6976; Zuckerman, R., et al., (1987) Nucleic Acids Res. 15:5305–5321.

In addition, procedures for the synthesis of oligonucleotides of desired sequence and containing phosphorothioate diesters by chemical sulfurization are well-established. The solid phase synthesis of random primers employs one or several specifically placed internucleotide phosphorothioate diesters at the 3'-end. Phosphorothioate triesters can be introduced by oxidizing the intermediate phosphite triester obtained during phosphoramidite chemistry with 3H-1, 2-benzodithiol-3-one 1,1 dioxide or Beaucage reagent to generate pentavalent phosphorous in which the phosphorothioate triester exists as a thione. The thione formed in this manner is stable to the subsequent oxidation steps necessary to generate internucleotidic phosphodiesters. (Iyer, R. P., et al. , J. Am. Chem. Soc., 112: 1253 (1990), and Iyer, et al., J. Org. Chem., 55: 4693 (1990)).

All references cited herein are incorporated by reference in their entirety to the extent not inconsistent with the disclosure herein.

Preferred embodiments described above are intended to be illustrative of the spirit of this invention. Numerous variations and applications will be readily apparent to those skilled in the art. The range and scope of this patent is defined by the following claims and their equivalents.

I claim:

1. A universal microarray comprising a solid substrate and a plurality of oligonucleotide probes wherein the plurality of oligonucleotide probes are bound on said substrate in a plurality of spots, wherein a pool of oligonucleotide probes of said plurality of oligonucleotide probes is bound to each spot of the microarray, each oligonucleotide of said plurality of oligonucleotide probes has the form:

B-C-D wherein
  a) portion B is a unique z-mer comprising from 5 to 8 nucleotide bases such that all $4^z$ permutations of A, G, C, and T are represented in said plurality of oligonucleotide probes;
  b) portion C is a variable x-mer comprising from 1 to 5 nucleotide bases such that all $4^x$ permutations of A, G, C, and T are represented in said plurality of oligonucleotide probes;
  c) portion D is a universal n-mer comprising from 5 to 8 nucleotide bases that is the same for every probe; and
wherein a pool of oligonucleotide probes contains oligonucleotide probes wherein only one of said $4^z$ permutation of B is present and all $4^x$ permutations of C are present in about equal concentrations.

2. The microarray of claim 1 wherein portions B, C, and D are joined in the 5'- to -3' direction or the 3'- to -5' direction, respectively.

3. The microarray of claim 1 wherein portions B, C and D are joined in the 5'–3' direction.

4. The microarray of claim 1 wherein z is 5 bases.

5. The microarray of claim 1 wherein z is 8 bases.

6. The microarray of claim 1 wherein portion B is a hexamer.

7. The microarray of claim 1 wherein n is 5 bases.

8. The microarray of claim 1 wherein n is 8 bases.

9. The microarray of claim 1 wherein portion D is a hexamer.

10. The microarray of claim 1 wherein portion C is a dimer.

11. The microarray of claim 1 wherein each oligonucleotide probe in said plurality of oligonucleotide probes further comprises a portion E that is a t-mer of 1 to 4 nucleotides adjacent to portion B or portion D at either the 5' end or the 3' end of each oligonucleotide probe wherein the sequence of portion E is variable within a pool of oligonucleotide probes such that all possible $4^t$ permutations of A, G, C, and T are represented within a pool of oligonucleotide probes for each permutation of B-C-D within that pool of oligonucleotide probes.

12. The microarray of claim 1 wherein each oligonucleotide probe of the plurality of probes further comprises a linker group A, for attachment of the probe to a substrate, bound at either the 5' or 3' end of probe.

13. The microarray of claim 1 wherein said substrate is chosen from the group consisting of polymers, glasses, semiconductors, papers, metals, gels and hydrogels.

14. The microarray of claim 13 wherein said substrate is further modified or coated to contain reactive functional groups.

15. The microarray of claim 13 wherein said substrate is glass.

16. The microarray of claim 15 wherein said glass is coated with a polymer or metal.

17. The microarray of claim 14 wherein said substrate or said coating on said substrate is gold or thiolated gold.

18. The microarray of claim 1 wherein the universal n-mer comprises about 40% to about 70% GC.

19. The microarray of claim 1 wherein the universal n-mer comprises greater than 50% GC.

20. The microarray of claim 1 wherein the number of spots of said plurality of spots is about 4096.

21. The microarray of claim 1 wherein said plurality of spots is segmented to form groups of spots.

22. The microarray of claim 21 wherein the number of spots per group of spots of said plurality of spots is less than 40.

23. The microarray of claim 21 wherein said groups are formed based on a physical property of the probes.

24. The microarray of claim 23 wherein said physical property is the theoretical melting temperature of the probes and their complements.

25. The microarray of claim 1 wherein z is 6, x is 2 and n is 6.

26. A universal microarray comprising a solid substrate and a plurality of oligonucleotide probes wherein the plurality of oligonucleotide probes are bound on said substrate in a plurality of spots, wherein a pool of oligonucleotide probes of said plurality of oligonucleotide probes is bound to each spot of the microarray, each oligonucleotide of said plurality of oligonucleotide probes has the form:

B-C-D wherein
a) portion B is a unique hexamer such that all $4^6$ permutations of A, G, C, and T are represented in said plurality of oligonucleotide probes;
b) portion C is a variable dimer such that all $4^2$ permutations of A, G, C, and T are represented in said plurality of oligonucleotide probes;
c) portion D is a universal hexamer that is the same for every probe; and
wherein a pool of oligonucleotide probes contains oligonucleotide probes wherein only one of said $4^6$ permutation of B is present and all $4^2$ permutations of C are present in about equal concentrations.

27. A method for determining relative gene expression between 2 or more test mixtures comprising:
a) providing a first set of a plurality of oligonucleotide primers having the form:

F-G wherein portion F is a universal n-mer comprising from 5 to 8 nucleotide bases and portion G is a variable x-mer comprising from 1 to 5 nucleotide base such that all $4^x$ permutations of A, G, C, and T are represented in about equal concentrations in said primer set;
b) separately contacting each of the populations of mRNA derived from each of the 2 or more test mixtures to each of the members of said set of primers to generate $4^x$ primed mRNA populations for each test mixture;
c) segregating the primed mRNA populations into one or more subsets of mRNA populations;
d) separately synthesizing cDNA populations from each of the primed mRNA populations in each subset of mRNA populations by reverse transcription;
e) recovering each of said synthesized cDNA populations with said primers attached thereto to obtain one or more cDNA subsets corresponding to the subsets of the primed mRNA populations from which they were derived;
f) differentially labeling each member of a subset of cDNA populations;
g) providing a microarray of claim 1 for each subset of cDNA populations, such that portions C and D of the probes of said microarray are the same length as and complementary to portions G and F, respectively, of the primer set used to synthesize the cDNA populations; such that all possible $4^x$ permutations of F-G are represented in about equal concentrations in said set of primers,
h) contacting one or more spots on a microarray with the differentially labeled members of a subset of cDNA populations such that each spot is contacted with all of the differentially labeled members of a subset of cDNA populations under conditions such that complementary cDNA and probe sequences hybridize;
i) repeating steps f–h for each subset of cDNA populations such that each subset of cDNA populations contacts a microarray not previously contacted with any other subset of cDNA populations;
j) detecting the signal generated from every spot on every array;
k) determining relative gene expression of the test mixtures by comparing the signal from a spot on one array to the corresponding spot on every other array wherein the probes on corresponding spots comprise the same unique z-mer, or comparing the signal from different labels on a single spot.

28. The method of claim 27 wherein said members of a cDNA subset are pooled prior to said step h).

29. The method of claim 27 wherein the amount of cDNA in each cDNA population is normalized relative to every other population prior to step h).

30. The method of claim 27 wherein after said step of recovering, the concentration of cDNA in each of said labeled cDNA populations is normalized such that the total amount of cDNA contacting the spots in the microarray is about equal for each of said labeled cDNA populations.

31. The method of claim 27 wherein said step of labeling occurs during synthesis of the cDNA populations.

32. The method of claim 31 wherein at least one of the dNTPs used for reverse transcription is present in a form that terminates cDNA synthesis.

33. The method of claim 32 wherein the dNTP that terminates cDNA population synthesis is labeled.

34. The method of claim 32 wherein cDNA is terminated at about 50 to about 100 bases.

35. The method of claim 31 wherein at least one of the dNTPs used for reverse transcription is present in labeled and unlabeled forms.

36. The method of claim 27 wherein cDNA is labeled after its synthesis.

37. The method of claim 27 wherein said cDNA is labeled with a label chosen from the group consisting of dyes, particles, and radioactive substances.

38. The method of claim 27 wherein said cDNA is labeled with a dye chosen from the group consisting of fluorescent, chemiluminescent, bioluminescent, and electroluminescent dyes.

39. The method of claim 27 wherein said cDNA is labeled with a radioactive label.

40. The method of claim 27 wherein said cDNA is labeled with a particle chosen from the group consisting of glass, silica, polymer, metal, and semiconductor particles.

41. The method of claim 27 further comprising:
a) providing a second set of microarrays and a second set of complementary primers wherein the complementary universal n-mers of the probes and primers in the second set are different from the universal n-mers of the first set;
b) performing steps a-k of claim 27 using said second set of microarrays and primers.

42. The method of claim 41 wherein the probes and primers in the second set have a different G C content than the probes and primers of the first set.

43. The method of claim 41 further comprising:
a) providing a third set of microarrays and a third set of complementary primers wherein the complementary universal n-mers of the probes and primers in the third set are different from the universal n-mers of the first and second sets;
b) performing steps a-k of claim 27 using said third set of microarrays and primers.

44. The method of claim 43 wherein the probes and primers in the third set have a different G C content than the probes and primers of the first set and the probes and primers of the second set.

45. A kit for determining or measuring relative gene expression between 2 or more test mixtures comprising:
a) one or more microarrays of claim 1;

b) one or more sets of primers, each primer having the form:

F-G wherein F is an n-mer comprising from 5 to 8 nucleotide bases and G is an x-mer comprising from 1 to 5 nucleotide bases which are the same length as and complementary to the universal n-mer D and variable x-mers C, respectively, of the probes on the one or more microarrays, such that all possible $4^x$ permutations of F-G are present in about equal concentrations in said set of primers.

46. The kit of claim 45 further comprising reagents for reverse transcription of mRNA populations from the 2 or more test mixtures to form cDNA populations.

47. The kit of claim 46 further comprising labels for differentially labeling the cDNA populations.

48. The kit of claim 47 further comprising instructions for binding cDNA to said microarrays and for determining relative gene expression based on said binding.

49. A set of oligonucleotide probes separated into a plurality of pools, each of said pools comprising a plurality of oligonucleotide probes, said oligonucleotide probes having the form:

B-C-D wherein
  a) portion B is a unique z-mer comprising from 5 to 8 nucleotide bases such that all $4^z$ permutations of A, G, C, and T are represented in said set of oligonucleotide probes and only one of said $4^z$ permutations is present in each pool;
  b) portion C is a variable x-mer comprising from 1 to 5 nucleotide bases such that all $4^x$ permutations of A, G, C, and T are represented in said set of oligonucleotide probes and all $4^z$ permutations are present in every pool in about equal concentrations; and
  c) portion D is a universal n-mer comprising from 5 to 8 nucleotide bases that is the same for every oligonucleotide probe.

50. The set of oligonucleotide probes of claim 49 further comprising a set of primers having the form

F-G wherein F is an n-mer comprising from 5 to 8 nucleotide bases and G is an x-mer comprising from 1 to 5 nucleotide bases wherein the F and G portions of the primer are the same length as and complementary to the universal n-mer D and variable x-mers C, respectively, of the such that all possible $4^x$ permutations of F-G are represented in about equal concentrations in said set of primers.

51. The combined sets of oligonucleotide probes and primers of claim 50
  wherein the universal n-mer of the probes is a hexamer and the variable x-mer of the probes is a dimer and F and G are complementary to the universal hexamer and variable dimer, respectively, of the such that all possible $4^2$ permutations of F-G are represented in about equal concentrations in said set of primers.

52. A set of oligonucleotide probes separated into a plurality of pools, each of said pools comprising a plurality of oligonucleotide probes, said oligonucleotide probes having the form:

B-C-D wherein
  a) portion B is a unique hexamer such that all $4^6$ permutations of A, G, C, and T are represented in said set of oligonucleotide probes and only one of said $4^6$ permutations is present in each pool;
  b) portion C is a variable dimer such that all $4^2$ permutations of A, G, C, and T are represented in said set of oligonucleotide probes and all $4^2$ permutations are present in every pool in about equal concentrations; and
  c) portion D is a universal hexamer that is the same for every oligonucleotide probe.

* * * * *